(12) United States Patent
Sano et al.

(10) Patent No.: US 11,166,639 B2
(45) Date of Patent: Nov. 9, 2021

(54) FLOW CONTROL VALVE AND BLOOD PRESSURE INFORMATION MEASUREMENT DEVICE HAVING THE SAME

(71) Applicant: OMRON HEALTHCARE Co., Ltd., Kyoto (JP)

(72) Inventors: Yoshihiko Sano, Kyoto (JP); Gaku Hasegawa, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 979 days.

(21) Appl. No.: 14/644,005

(22) Filed: Mar. 10, 2015

(65) Prior Publication Data

US 2015/0182133 A1    Jul. 2, 2015

Related U.S. Application Data

(63) Continuation of application No. PCT/JP2013/070329, filed on Jul. 26, 2013.

(30) Foreign Application Priority Data

Sep. 11, 2012    (JP) .............................. JP2012-199617

(51) Int. Cl.
*A61B 5/02* (2006.01)
*A61B 5/0235* (2006.01)
(Continued)

(52) U.S. Cl.
CPC .............. *A61B 5/0235* (2013.01); *F16K 1/36* (2013.01); *F16K 1/42* (2013.01); *F16K 25/00* (2013.01);
(Continued)

(58) Field of Classification Search
CPC . A61B 5/0235; A61B 17/132; A61B 17/1322; A61B 17/135; A61B 17/1355
See application file for complete search history.

(56) References Cited

U.S. PATENT DOCUMENTS 3,424,951 A * 1/1969 Barker ................ F16K 31/0693
361/170
4,245,815 A * 1/1981 Willis ................ F16K 31/0658
137/903
(Continued)

FOREIGN PATENT DOCUMENTS

CN      1434907 A    8/2003
JP    S6059873 U    4/1985
(Continued)

OTHER PUBLICATIONS

Office Action in counterpart Japanese Patent Application No. 2012-199617 dated Jul. 19, 2016 (14 pages).
(Continued)

*Primary Examiner* — Christian Jang
(74) *Attorney, Agent, or Firm* — Osha Bergman Watanabe & Burton

(57) ABSTRACT

A flow control valve includes a bobbin around which a solenoid coil is wound, a plunger inserted into the bobbin so as to be capable of sliding, a core in which is provided an outflow port from which a fluid flows, a spring that biases the plunger in a direction away from the core, and a valve body incorporated into the plunger so as to be disposed facing the outflow port. During a non-operating state, the valve body is disposed at a first position distanced from the outflow port. During an operating state, the plunger is pulled toward the core against a biasing force of the spring, and is not in contact with the core when the valve body is at a second position in which the valve body blocks the outflow port.

5 Claims, 25 Drawing Sheets

(51) Int. Cl.
*F16K 1/36* (2006.01)
*F16K 31/06* (2006.01)
*F16K 1/42* (2006.01)
*F16K 25/00* (2006.01)

(52) U.S. Cl.
CPC ...... *F16K 31/0655* (2013.01); *F16K 31/0658* (2013.01)

(56) References Cited

U.S. PATENT DOCUMENTS

| | | | | |
|---|---|---|---|---|
| 5,110,087 | A * | 5/1992 | Studtmann | H01F 7/13 251/129.16 |
| 5,440,925 | A * | 8/1995 | Padden | G01F 1/90 73/1.19 |
| 5,730,139 | A * | 3/1998 | Miyazaki | A61B 5/0225 600/493 |
| 6,262,994 | B1 * | 7/2001 | Dirschedl | H04L 1/0003 370/465 |
| 7,049,917 | B2 * | 5/2006 | Sano | A61B 5/0235 251/129.15 |
| 2003/0120157 | A1 * | 6/2003 | Fukui | A61B 5/0235 600/484 |
| 2006/0155197 | A1 * | 7/2006 | Kishimoto | A61B 5/02141 600/498 |
| 2010/0324429 | A1 * | 12/2010 | Leschinsky | A61B 5/02208 600/493 |

FOREIGN PATENT DOCUMENTS

| | | |
|---|---|---|
| JP | S60-142370 U | 9/1985 |
| JP | H09-135817 A | 5/1997 |
| JP | 2004-185268 A | 7/2004 |
| JP | 2006-029362 A | 2/2006 |
| JP | 2006-075439 A | 3/2006 |
| JP | 2006-242232 A | 9/2006 |
| JP | 2009219661 A | 10/2009 |
| JP | 2010-207509 A | 9/2010 |

OTHER PUBLICATIONS

Office Action in counterpart Chinese Patent Application No. 201380047063.6, dated Dec. 18, 2015 (15 pages).
International search report dated Sep. 17, 2013 in related International Application No. PCT/JP2013/070329 (4 pages).

* cited by examiner

FLOW CONTROL VALVE AND BLOOD PRESSURE INFORMATION MEASUREMENT DEVICE HAVING THE SAME

TECHNICAL FIELD

The present invention relates to flow control valves capable of controlling a flow rate of a fluid in a variable manner, and to blood pressure information measurement devices having the same. The present invention particularly relates to solenoid-type flow control valves and blood pressure information measurement devices having such solenoid-type flow control valves as exhaust valves for reducing the internal pressure of a pressurizing fluid bladder.

BACKGROUND ART

Measuring the blood pressure information of a measurement subject is extremely important in understanding the health of the measurement subject. In addition to measuring systolic blood pressure values and diastolic blood pressure values, whose usefulness as a representative index in analyzing the risk of stroke, cardiovascular disease such as heart failure and myocardial infarction, and the like is widely accepted, attempts are being made in recent years to understand burdens on the heart, degrees of artery hardness, and so on by measuring the pulse waves of measurement subjects.

Blood pressure information measurement devices are devices for measuring such blood pressure information, and such devices are expected to have a further role in the early detection, prevention, and treatment of cardiovascular disease. Note that various types of circulatory system information generally fall under the umbrella of "blood pressure information", including such various indexes as the systolic blood pressure value, diastolic blood pressure value, average blood pressure value, pulse wave, pulse beat, artery hardness, and so on.

Generally speaking, a blood pressure information measurement device cuff (called simply a "cuff" hereinafter) is used in the measurement of blood pressure information. Here, "cuff" refers to a band-shaped or ring-shaped structure, containing a fluid bladder having an interior cavity, that can be affixed to part of a body, and is used to measure blood pressure information by injecting a fluid such as a gas, a liquid, or the like into the interior cavity so as to cause the fluid bladder to expand and compress an artery.

Normally, a blood pressure information measurement device is provided with a pressure pump and an exhaust valve as a pressurizing/depressurizing mechanism for increasing/reducing the internal pressure in the fluid bladder. Of these, the exhaust valve is for maintaining the internal pressure of the fluid bladder inflated by the pressure pump when in a closed state, and for deflating the fluid bladder when in an open state. A flow control valve capable of controlling an exhaust flow rate in a variable manner by controlling the valve operations when reducing the internal pressure of the fluid bladder can be used favorably as such an exhaust valve.

A system that controls an outflow rate by providing a valve body opposing an outflow port and controlling a distance between the outflow port and the valve body in a variable manner by sliding the valve body using a mobile shaft is used as such a flow control valve. This type of flow control valve is broadly divided into linear-type flow control valves and solenoid-type flow control valves depending on the driving system used therein.

The linear-type flow control valve is a type that uses a permanent magnet and an electromagnetic coil and causes the mobile shaft to slide by providing one of the permanent magnet and the electromagnetic coil on the mobile shaft. The solenoid-type flow control valve, meanwhile, is a type that uses a plunger (moving core) as the mobile shaft, a core (fixed core) provided with an outflow port, and a solenoid coil, and causes the plunger to slide using the solenoid coil.

Of these, the linear-type flow control valve has a comparatively complicated device configuration, and thus it is difficult to make the device lighter and smaller; furthermore, because the device requires a strong permanent magnet, the manufacturing costs are high. On the other hand, the solenoid-type flow control valve has a comparatively simple device configuration, and can thus be made lighter and smaller; furthermore, the device does not require a permanent magnet, and thus there is an advantage that the manufacturing cost can be reduced.

The solenoid-type flow control valve is thus particularly favorable as a flow control valve provided in a blood pressure information measurement device. JP H9-135817A (Patent Literature 1), JP 2004-185268A (Patent Literature 2), JP 2006-29362A (Patent Literature 3), and so on, for example, are documents disclosing specific configurations of solenoid-type flow control valves.

CITATION LIST

Patent Literature

Patent Literature 1: JP H9-135817A
Patent Literature 2: JP 2004-185268A
Patent Literature 3: JP 2006-29362A

SUMMARY OF INVENTION

However, conventional solenoid-type flow control valves, such as those disclosed in the aforementioned Patent Literature, have not necessarily been able to sufficiently handle the sort of precise flow rate control required in blood pressure information measurement devices.

That is, in a solenoid-type flow control valve, a magnetic flux is produced by electrifying the solenoid coil, and the plunger is pulled toward (adheres to) the core as a result, which causes the plunger to slide; an adhesion force produced at that time (to rephrase, a driving force of the plunger) is inversely proportional to the square of the distance between the core and the plunger due to changes in the magnetic flux density.

Accordingly, in a range where the flow rate can actually be controlled, where the core and plunger have approached one another and the core-plunger distance is extremely low, a high driving force is obtained for the plunger; however, when the flow rate is changed by changing a driving voltage and causing the plunger to move, changing the driving voltage even slightly causes drastic increases and decreases in the plunger driving force and the distance the plunger moves. It is thus difficult to precisely control the driving force and movement distance of the plunger, and thus in actuality, precise flow rate control cannot be carried out.

As a result, in a blood pressure information measurement device provided with a conventional solenoid-type flow control valve as described above, the inflation and deflation of the pressurizing fluid bladder cannot be controlled in a sufficiently precise manner using only that valve; as such, it has been typical to implement a configuration in which the flow control valve is used only as a simple rapid exhaust valve and a flow control mechanism including a slow exhaust valve employing a rubber valve or the like is provided separately.

However, in the case where the blood pressure information measurement device is configured in this manner, the device configuration will naturally become complicated, which is disadvantageous in terms of reducing the size and weight of the device, cutting manufacturing costs, and so on.

Therefore, one or more embodiments of the present invention provides a solenoid-controlled flow control valve capable of precise flow rate control, and also provides a blood pressure information measurement device that has a simple configuration and is capable of precisely controlling the internal pressure of a pressurizing fluid bladder by providing the aforementioned flow control valve as an exhaust valve.

A flow control valve according to one or more embodiments of the present invention is capable of controlling a flow rate of a fluid in a variable manner, and includes a solenoid coil for generating a magnetic flux, a bobbin around which the solenoid coil is wound, a plunger inserted into the bobbin so as to be capable of sliding, a core in which is provided an outflow port from which the fluid flows, a biasing mechanism configured to bias the plunger in a direction away from the core, and a valve body disposed facing the outflow port. During a non-operating state in which the solenoid coil is not electrified, the valve body is disposed at a first position distanced from the outflow port. In the aforementioned flow control valve according to one or more embodiments of the present invention, during an operating state in which the solenoid coil is electrified, a flow rate of the fluid flowing from the outflow port is adjusted by the valve body being moved in a direction toward the outflow port due to the plunger being driven against a biasing force of the biasing mechanism and a distance between the valve body and the outflow port changing as a result. In the aforementioned flow control valve according to one or more embodiments of the present invention, when the valve body is at a second position in which the valve body blocks the outflow port, the plunger is not in contact with the core.

In the aforementioned flow control valve according to one or more embodiments of the present invention, when the valve body is at a third position in which the valve body controls the flow rate, the plunger is disposed between a position of the plunger when the valve body is at the first position and a position of the plunger when the valve body is at the second position.

In the aforementioned flow control valve according to one or more embodiments of the present invention, when the valve body is at the second position, a distance between the plunger and the core is greater than or equal to 0.2 mm.

In the aforementioned flow control valve according to one or more embodiments of the present invention, the valve body is incorporated into the plunger by being affixed to a main surface of the plunger that faces the core. In this case, at least part of the valve body is positioned so as to project toward the core beyond the main surface of the plunger that faces the core.

In the aforementioned flow control valve according to one or more embodiments of the present invention, the valve body may be incorporated into the core by affixing part of the valve body to the core.

In the aforementioned flow control valve according to one or more embodiments of the present invention, the valve body is configured of an elastic member.

In the aforementioned flow control valve according to one or more embodiments of the present invention, a main surface of the valve body that faces the outflow port is slanted relative to the outflow port.

In the aforementioned flow control valve according to one or more embodiments of the present invention, the main surface of the valve body that faces the outflow port has minute non-planarities.

In the aforementioned flow control valve according to one or more embodiments of the present invention, at least one of the main surface of the plunger that faces the core and a main surface of the core that faces the plunger has a recessed shape, and the other of the main surface of the plunger that faces the core and the main surface of the core that faces the plunger has a protruding shape.

A blood pressure information measurement device according to one or more embodiments of the present invention includes the aforementioned flow control valve according to one or more embodiments of the present invention as an exhaust valve for reducing an internal pressure of a pressurizing fluid bladder for compressing a body.

In the aforementioned blood pressure information measurement device according to one or more embodiments of the present invention, during measurement, at least a systolic blood pressure value and a diastolic blood pressure value are calculated based on a deflation measurement method by controlling the driving of the flow control valve serving as the exhaust valve so that the internal pressure of the pressurizing fluid bladder decreases slowly, and after the measurement is complete, the driving of the flow control valve serving as the exhaust valve is controlled so that the internal pressure of the pressurizing fluid bladder decreases rapidly.

In the aforementioned blood pressure information measurement device according to one or more embodiments of the present invention, during measurement, at least a systolic blood pressure value and a diastolic blood pressure value are calculated based on an inflation measurement method by controlling the driving of the flow control valve serving as the exhaust valve so that the internal pressure of the pressurizing fluid bladder increases slowly; and after the measurement is complete, the driving of the flow control valve serving as the exhaust valve is controlled so that the internal pressure of the pressurizing fluid bladder decreases rapidly.

According to one or more embodiments of the present invention, it is possible to provide a solenoid-controlled flow control valve capable of precise flow rate control, and also to provide a blood pressure information measurement device that has a simple configuration and is capable of precisely controlling the internal pressure of a pressurizing fluid bladder by providing the aforementioned flow control valve as an exhaust valve.

DETAILED DESCRIPTION OF INVENTION

Figure 1:
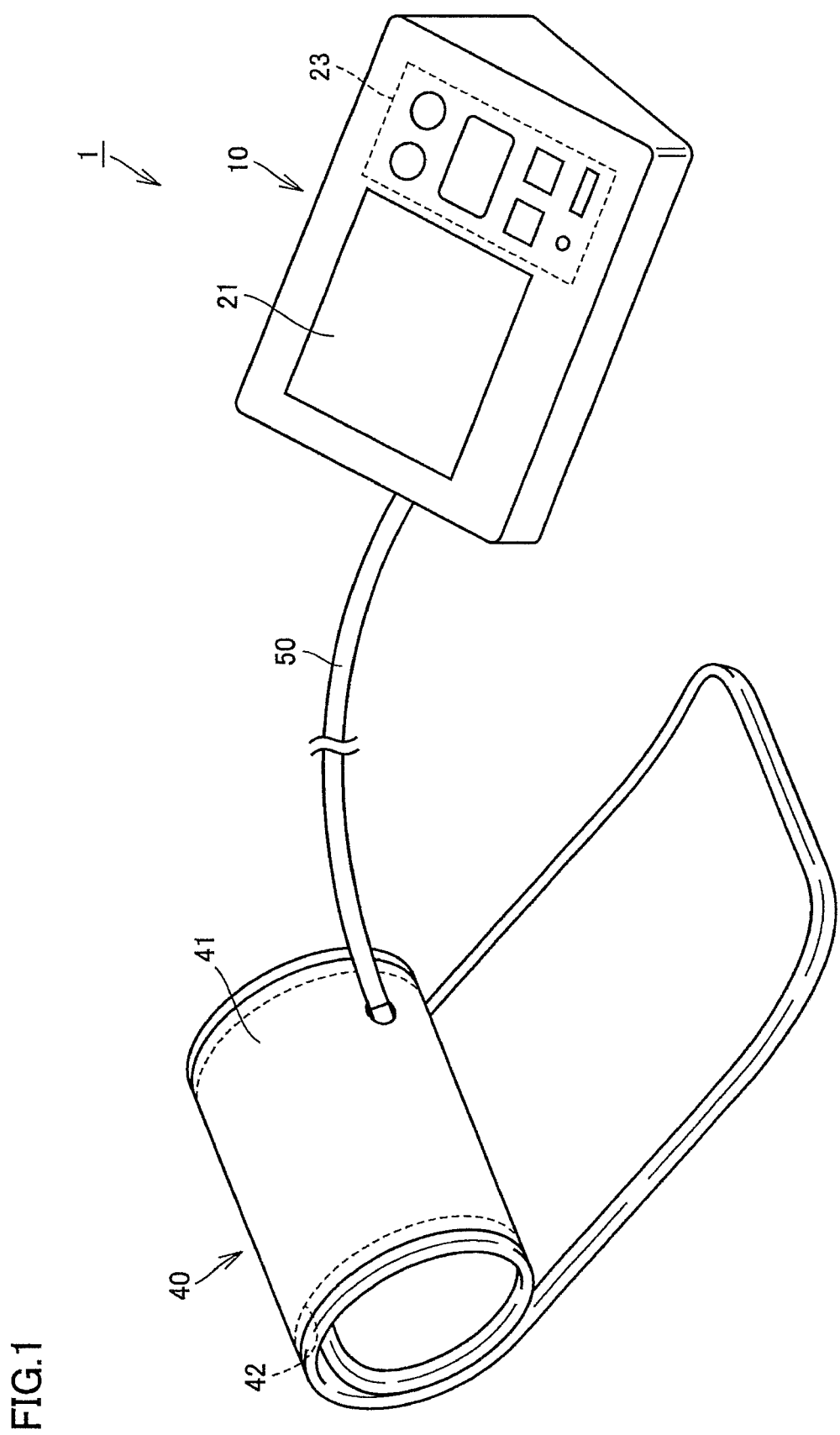
FIG. 1 is a perspective view illustrating the external structure of a blood pressure monitor according to a first embodiment of the present invention.

Hereinafter, embodiments of the present invention will be described in detail with reference to the drawings. The following embodiments will describe what is known as an upper arm blood pressure monitor, configured to be capable of measuring a systolic blood pressure value and a diastolic blood pressure value of a measurement subject by using a cuff affixed to the upper arm of the measurement subject, as an example of a blood pressure information measurement device. Note that in the following embodiments, identical or common elements are given the same reference numerals in the drawings, and descriptions thereof will not be repeated.

First Embodiment

Figure 2:
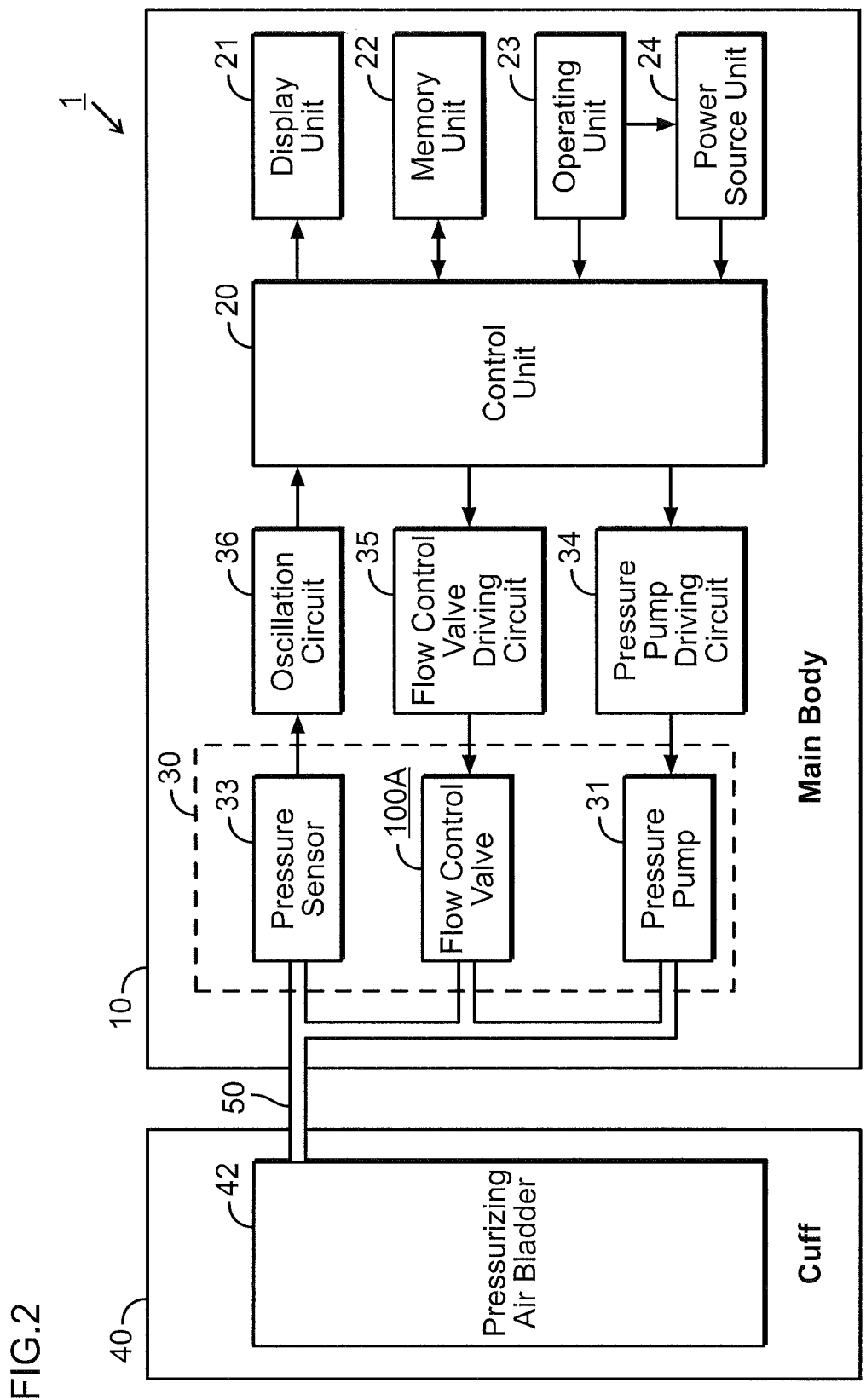
FIG. 2 is a diagram illustrating a functional block configuration of the blood pressure monitor according to the first embodiment of the present invention.

FIG. 1 is a perspective view illustrating the external structure of a blood pressure monitor according to a first embodiment of the present invention, and FIG. 2 is a diagram illustrating a functional block configuration thereof. First, the configuration of a blood pressure monitor 1 according to the present embodiment will be described with reference to FIGS. 1 and 2.

As shown in FIG. 1, the blood pressure monitor 1 according to the present embodiment includes a main body 10, a cuff 40, and an air tube 50. The main body 10 includes a box-shaped housing, and a display unit 21 and an operating unit 23 are provided on the top surface thereof. During measurement, the main body 10 is used by being placed on a placement surface such as a table or the like. The cuff 40 primarily includes a band-shaped and bladder-shaped outer cover 41 and a pressurizing air bladder 42 that is contained in the outer cover 41 and serves as a pressurizing fluid bladder; the cuff 40 has an overall ring-shaped form. During measurement, the cuff 40 is used by being wrapped around and worn on the upper arm of a measurement subject. The air tube 50 connects the main body 10 and the cuff 40, which are configured as separate entities.

As shown in FIG. 2, in addition to the aforementioned display unit 21 and operating unit 23, the main body 10 includes a control unit 20, a memory unit 22, a power source unit 24, a pressure pump 31, a flow control valve 100A serving as an exhaust valve, a pressure sensor 33, a pressure pump driving circuit 34, a flow control valve driving circuit 35, and an oscillation circuit 36. The pressure pump 31, the flow control valve 100A, and the pressure sensor 33 correspond to a pressurizing air system component 30 provided in the blood pressure monitor 1, and the pressure pump 31 and the flow control valve 100A in particular correspond to a pressurizing/depressurizing mechanism for increasing/reducing an internal pressure of the pressurizing air bladder 42.

The pressurizing air bladder 42 pressurizes the upper arm when worn thereon, and has an interior cavity. The pressurizing air bladder 42 is connected to the pressure pump 31, the flow control valve 100A, and the pressure sensor 33 respectively, which correspond to the aforementioned pressurizing air system component 30, via the aforementioned air tube 50. As a result, the pressurizing air bladder 42 is inflated and expands under the driving of the pressure pump 31; the internal pressure is held, the pressurizing air bladder 42 is deflated and contracts, and so on by controlling the driving of the flow control valve 100A serving as the exhaust valve.

The control unit 20 is configured of a CPU (central processing unit), for example, and is a unit for controlling the blood pressure monitor 1 as a whole. The display unit 21 is configured of an LCD (liquid-crystal display), for example, and is a unit for displaying measurement results and the like. The memory unit 22 is configured of a ROM (read-only memory), a RAM (random access memory), or the like, for example, and stores programs for causing the control unit 20 and the like to execute processes for measuring a blood pressure value, stores measurement results, and so on. The operating unit 23 is a unit for accepting operations made by a measurement subject or the like and inputting such external commands into the control unit 20, the power source unit 24, and the like. The power source unit 24 is a unit for supplying electricity to the control unit 20.

The control unit 20 inputs control signals for driving the pressure pump 31 and the flow control valve 100A into the pressure pump driving circuit 34 and the flow control valve driving circuit 35, respectively, inputs blood pressure values serving as measurement results to the display unit 21 and the memory unit 22, and so on. The control unit 20 also includes a blood pressure information obtainment unit (not shown) that obtains a measurement subject's blood pressure value based on a pressure value detected by the pressure sensor 33, and the blood pressure value obtained by the blood pressure information obtainment unit is inputted into the aforementioned display unit 21 and memory unit 22 as a measurement result. Note that the blood pressure monitor 1 may also include a separate output unit that outputs a blood pressure value to an external device (for example, a PC (personal computer), a printer, or the like) as the measurement result. For example, a serial communication line, a device that writes to various types of recording media, or the like can be used as the output unit.

The pressure pump driving circuit 34 controls the operations of the pressure pump 31 based on the control signal inputted from the control unit 20. The flow control valve driving circuit 35 controls opening/closing operations of the flow control valve 100A based on the control signal inputted from the control unit 20. The pressure pump 31 increases the internal pressure of the pressurizing air bladder 42 (called the "cuff pressure" as well hereinafter) by supplying air to the interior cavity of the pressurizing air bladder 42, and the operations thereof are controlled by the aforementioned pressure pump driving circuit 34. The flow control valve 100A maintains the internal pressure of the pressurizing air bladder 42, reduces the cuff pressure by opening the interior cavity of the pressurizing air bladder 42 to the exterior, and so on, and the operations thereof are controlled by the aforementioned flow control valve driving circuit 35. The pressure sensor 33 detects the internal pressure of the pressurizing air bladder 42 and inputs, to the oscillation circuit 36, an output signal based on the detected pressure. The oscillation circuit 36 generates an oscillation frequency signal in accordance with the signal inputted from the pressure sensor 33, and inputs the generated signal to the control unit 20.

Figure 3:
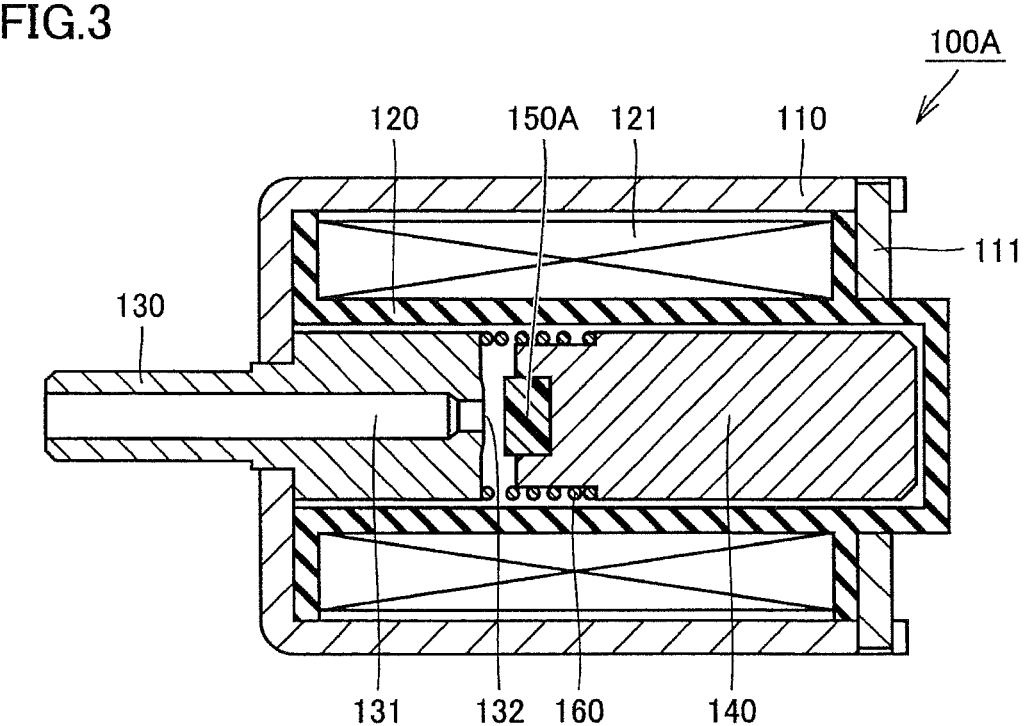
FIG. 3 is a schematic cross-sectional view of a flow control valve according to the first embodiment of the present invention.

FIG. 3 is a schematic cross-sectional view of the flow control valve according to the present embodiment. Next, the specific configuration of the flow control valve 100A according to the present embodiment will be described with reference to FIG. 3. Note that the flow control valve 100A according to the present embodiment is a normally-open solenoid-type flow control valve in which an outflow port 132, mentioned later, is completely open when not operating.

As shown in FIG. 3, the flow control valve 100A according to the present embodiment primarily includes a frame 110 and a base 111 serving as a casing, a bobbin 120, a solenoid coil 121, a core 130, a plunger 140, a valve body 150A, and a spring 160 serving as a biasing mechanism.

The frame 110 is a member that defines one end surface in an axial direction of the approximately rectangular flow control valve 100A and a pair of opposing side surfaces that configure a peripheral surface of the flow control valve 100A, whereas the base 111 is a member that defines another end surface in the axial direction of the flow control valve 100A. The frame 110 and the base 111 are configured as an integrated body through crimping, welding, or the like.

The frame 110 and the base 111 are both members configured of a soft magnetic material, and, according to one or more embodiments of the present invention, may be configured of an electromagnetic steel sheet having high magnetic permeability, a cold-rolled steel sheet (SPCC-SD), or the like. The frame 110 and the base 111 not only configure a hull for the flow control valve 100A, but also fill a role of a yoke that adjusts the paths of magnetic flux lines produced when the solenoid coil 121 is electrified.

The bobbin 120 is housed within a space enclosed by the frame 110 and the base 111. The bobbin 120 is a cylindrical member configured of a nonmagnetic material, and is configured of a resinous member as exemplified by polybutylene terephthalate. The bobbin 120 is disposed coaxially with the flow control valve 100A so that an axis line of the bobbin 120 matches an axis line of the flow control valve 100A. The bobbin 120 is a member for supporting the solenoid coil 121, and is also a member for defining a path along with the plunger 140 moves.

The solenoid coil 121 is formed by winding a conductive wire such as a copper wire (a coiled wire) around a circumferential surface of the bobbin 120, and produces a magnetic flux when electrified. Note that both ends of the conductive wire that configures the solenoid coil 121 are connected to lead wires or the like (not shown), and a current for driving is applied to the solenoid coil 121 via the lead wires.

The core 130 is configured of an approximately cylindrical member inside of which is provided a nozzle portion 131 through which a fluid flows; the core 130 is affixed to the frame 110 through crimping, welding, or the like so as to penetrate through a wall portion that defines one of the aforementioned end surfaces of the frame 110. The core 130 is disposed coaxially with the flow control valve 100A so that an axis line of the core 130 matches the axis line of the flow control valve 100A.

Figure 4:
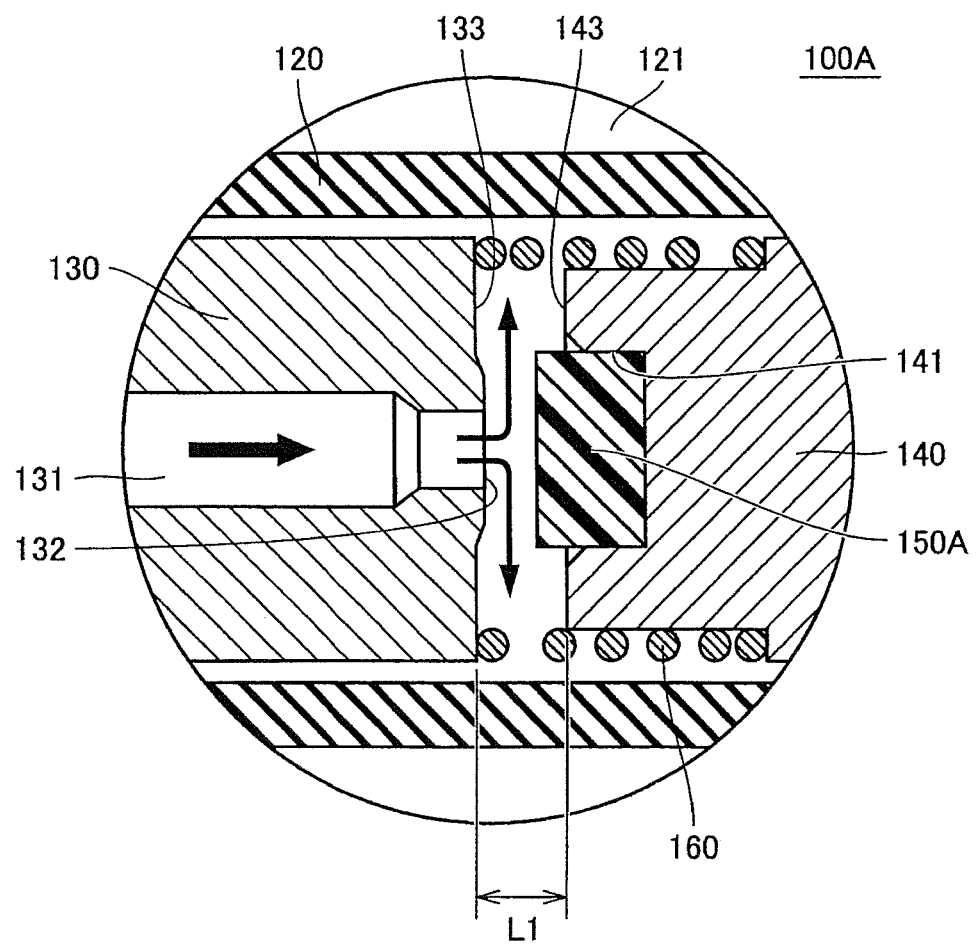
FIG. 4 is an enlarged cross-sectional view of primary components, illustrating the flow control valve shown in FIG. 3 in an open state.
Figure 5:
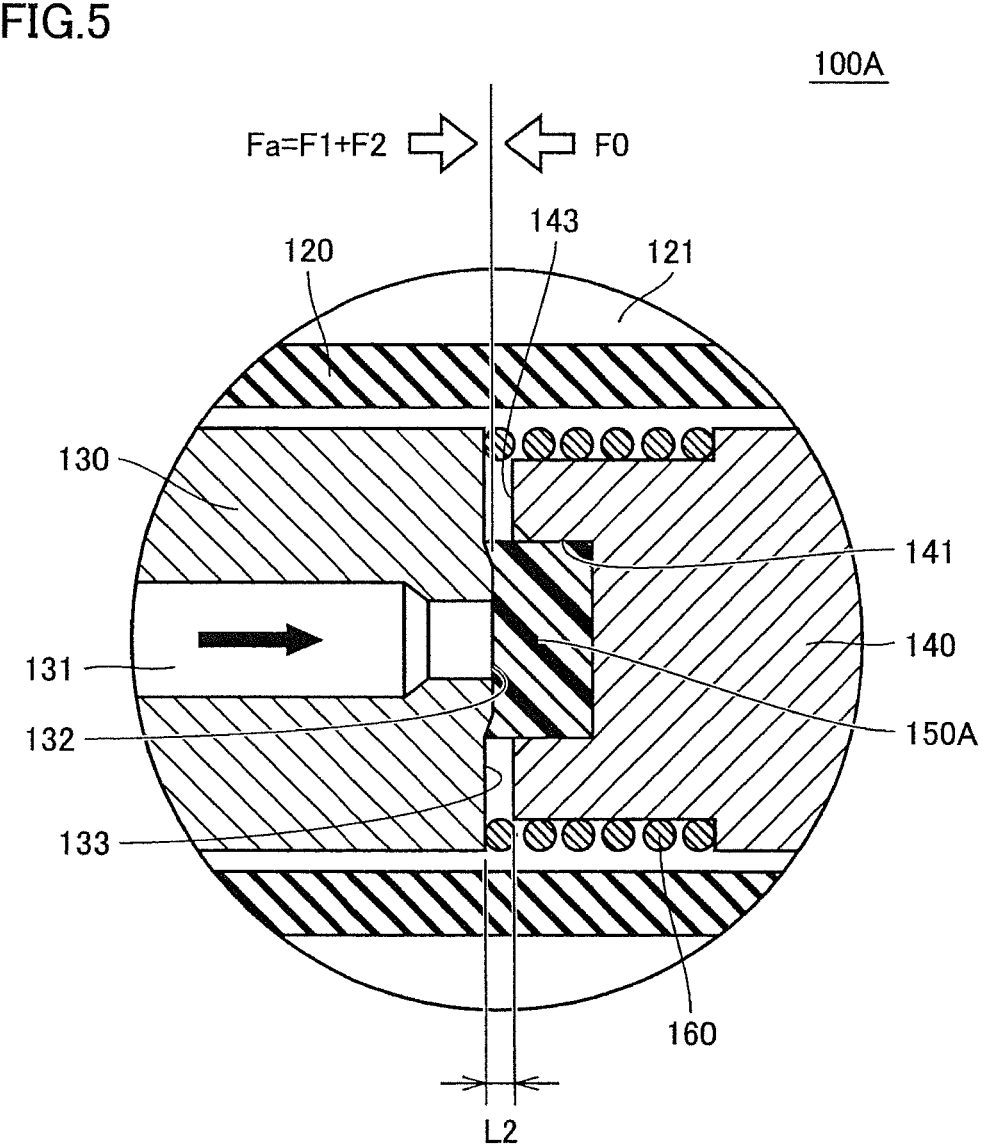
FIG. 5 is an enlarged cross-sectional view of primary components, illustrating the flow control valve shown in FIG. 3 in a closed state.
Figure 6:
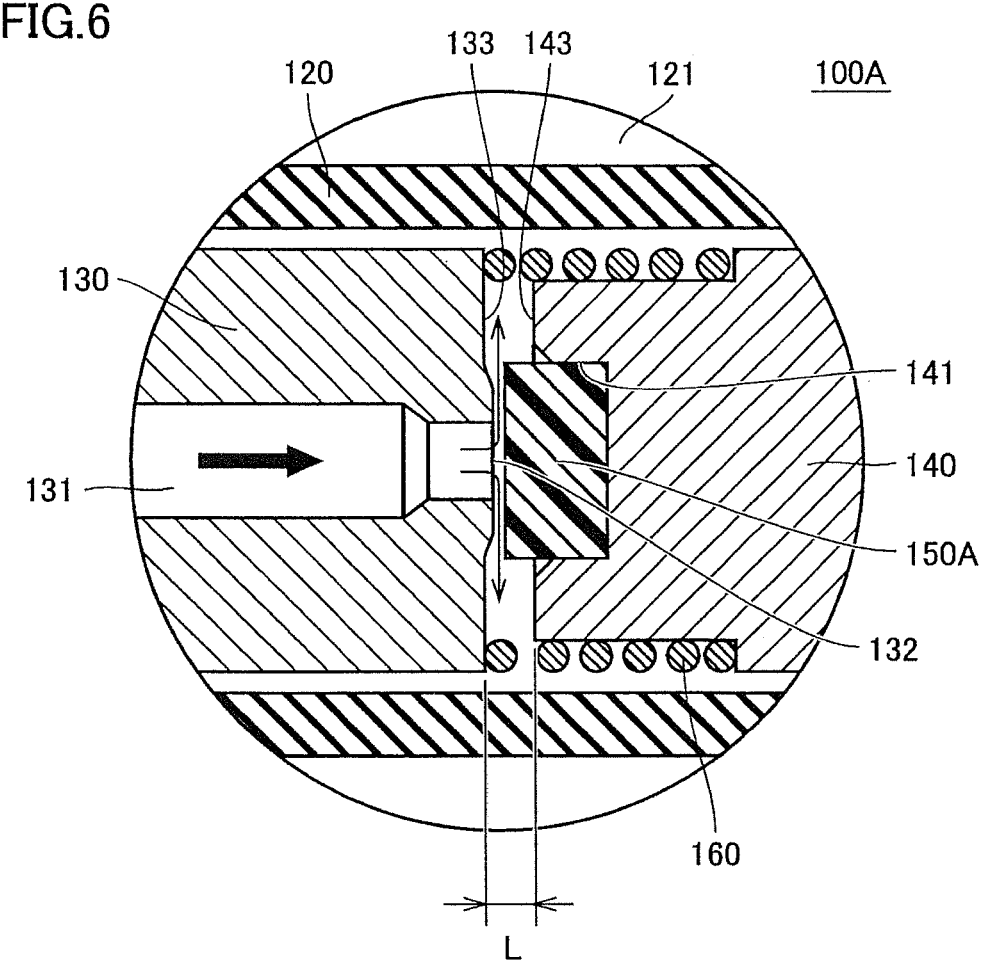
FIG. 6 is an enlarged cross-sectional view of primary components, illustrating the flow control valve shown in FIG. 3 in a limited flow state.

One end portion of the core 130 that is located in the interior of the casing is housed within the bobbin 120, and the outflow port 132, which communicates with the aforementioned nozzle portion 131, is provided in an axial direction end surface 133 that corresponds to a leading end surface of the core 130 (see FIGS. 4 through 6). The outflow port 132 is a member for exhausting the fluid to the exterior when in an open state.

Figure 11:
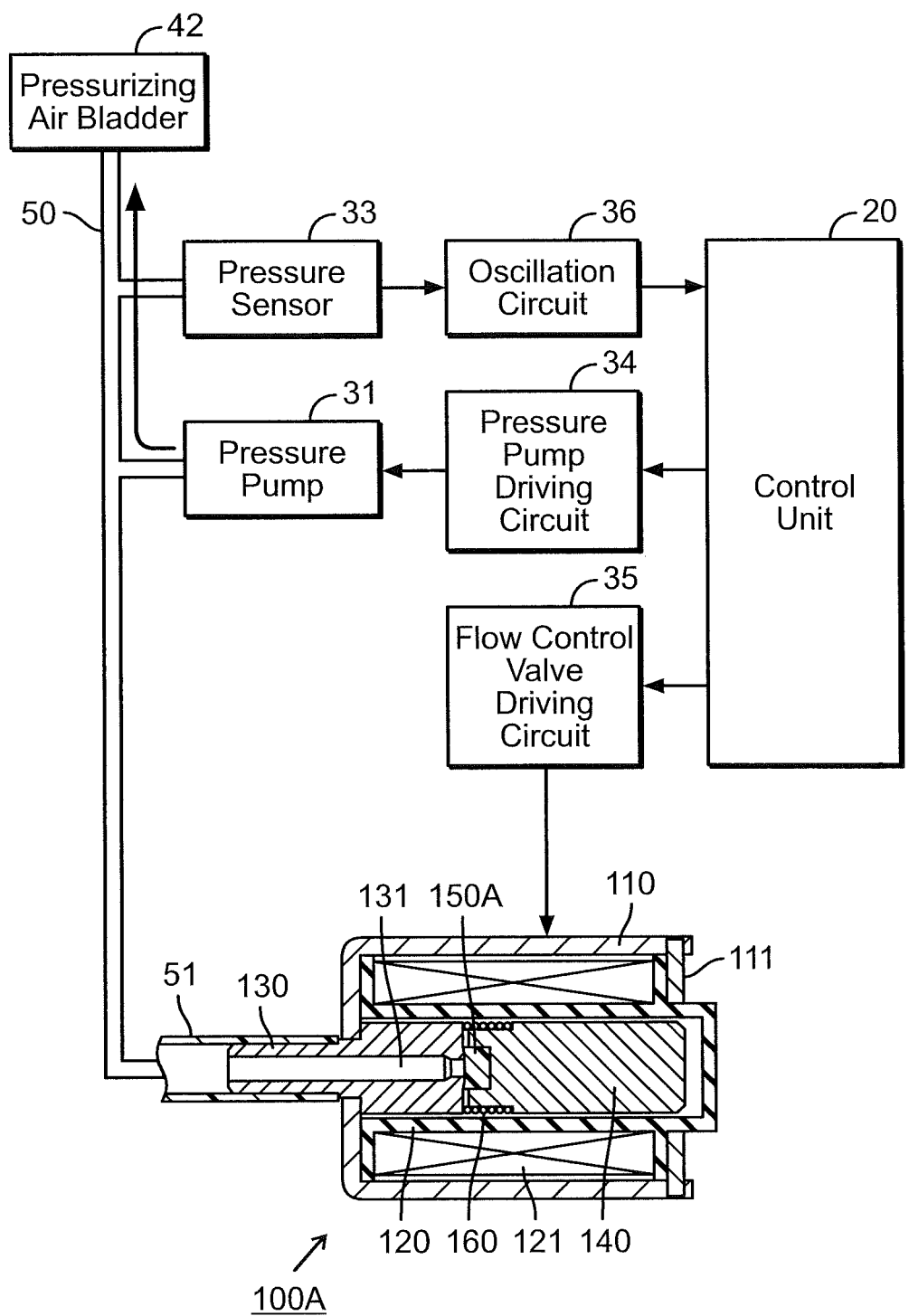
FIG. 11 is a diagram illustrating specific operations performed during rapid inflation, in the case where the operational flow shown in FIG. 10 is carried out by the blood pressure monitor according to the first embodiment of the present invention.
Figure 12:
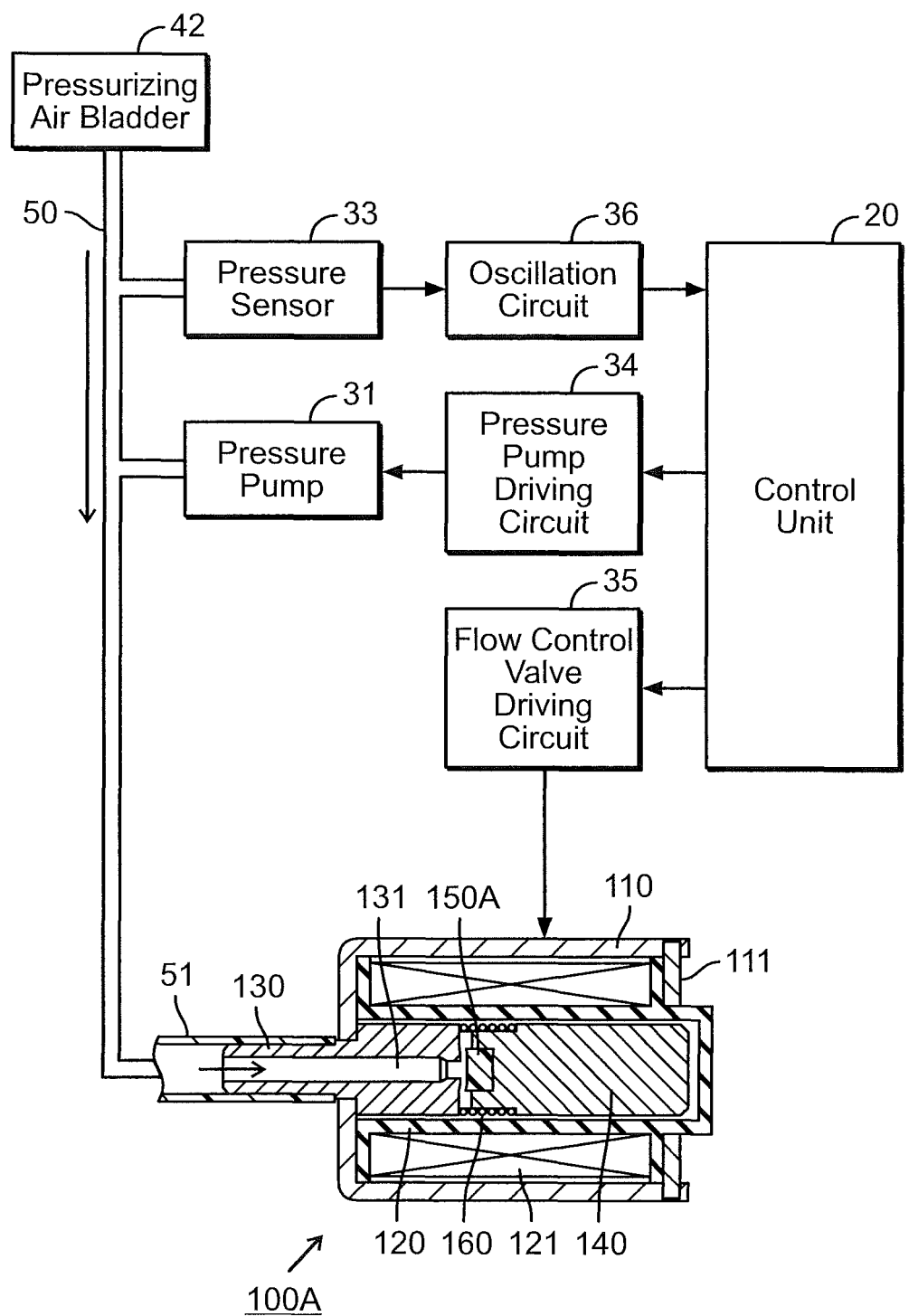
FIG. 12 is a diagram illustrating specific operations performed during slow deflation, in the case where the operational flow shown in FIG. 10 is carried out by the blood pressure monitor according to the first embodiment of the present invention.
Figure 13:
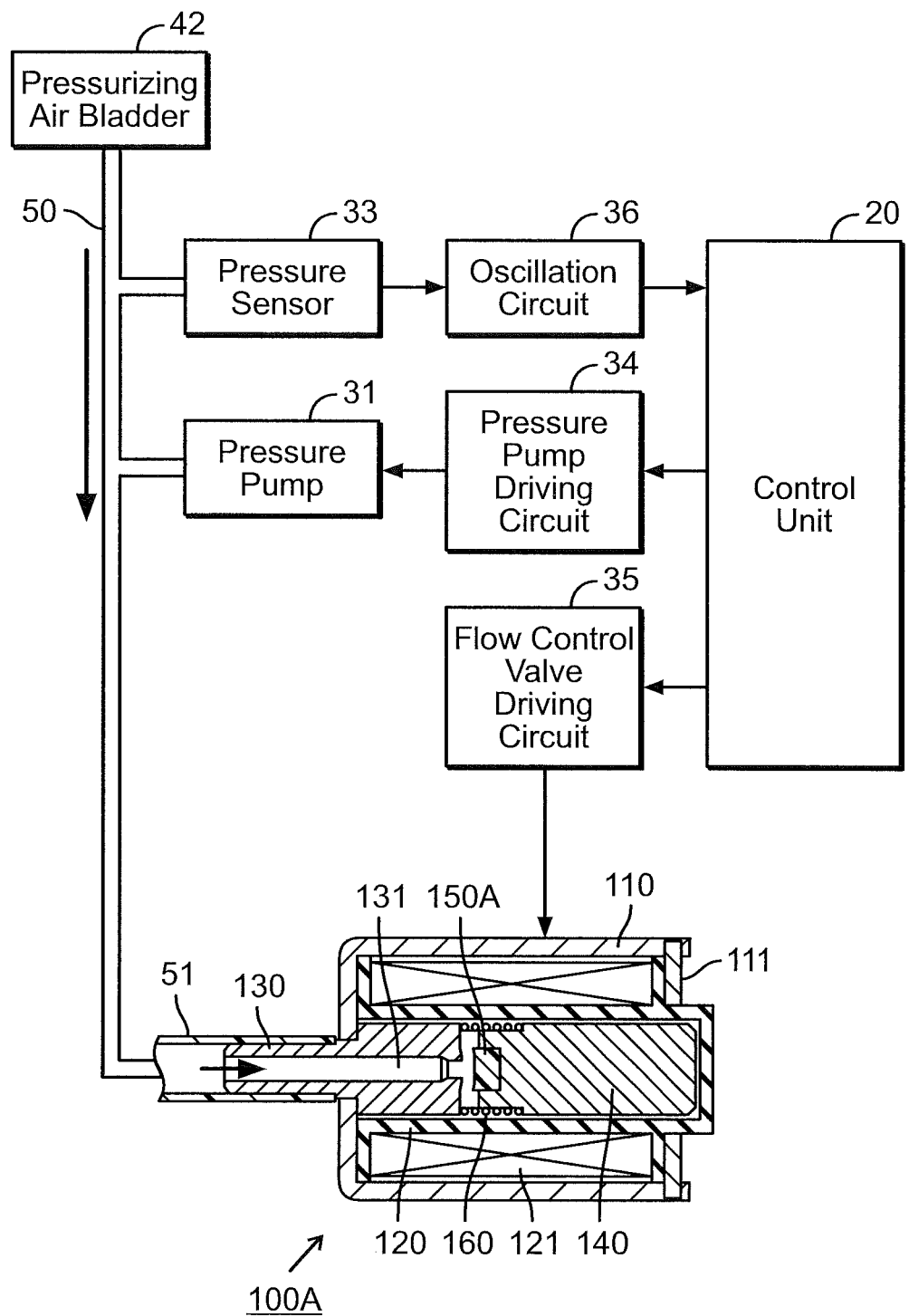
FIG. 13 is a diagram illustrating specific operations performed during rapid deflation, in the case where the operational flow shown in FIG. 10 is carried out by the blood pressure monitor according to the first embodiment of the present invention.

Meanwhile, the other end portion of the core 130 that is located on the outside of the casing is connected to a connecting tube 51, and the nozzle portion 131 is connected to the air tube 50, which is in turn connected to the pressurizing air bladder 42, via the connecting tube 51 (see FIGS. 11 to 13). Through this, the outflow port 132 communicates with the pressurizing air bladder 42 via the nozzle portion 131, the connecting tube 51, and the air tube 50.

The core 130 is a member configured of a soft magnetic material, and, according to one or more embodiments of the present invention, is configured of electromagnetic steel, sulfur composite free-cutting steel (SUM24L), or the like. The core 130 configures a fixed core, and pulls the plunger 140 when the solenoid coil 121 is electrified and a magnetic flux passes through the core 130.

The plunger 140 is an approximately cylindrical member, and is housed within the bobbin 120 by being inserted therein in a slidable state. The plunger 140 is disposed coaxially with the flow control valve 100A so that an axis line of the plunger 140 matches the axis line of the flow control valve 100A, and is also disposed coaxially with the core 130 as a result. A housing recess portion 141 (see FIGS. 4 through 6) for housing the valve body 150A is provided in a location, of an axial direction end surface 143 of the plunger 140 that faces the core 130 (see FIGS. 4 through 6), that corresponds to the aforementioned outflow port 132.

The plunger 140 is a member configured of a soft magnetic material, and, according to one or more embodiments of the present invention, is configured of electromagnetic steel, sulfur composite free-cutting steel (SUM24L), or the like. The plunger 140 configures a moving core, and slides along the interior of the bobbin 120 when pulled by the core 130 as a result of a magnetic flux passing therethrough when the solenoid coil 121 is electrified.

The valve body 150A is configured as an elastic member configured of silicone rubber, a nitrile rubber as exemplified by NBR, or the like, and has an approximately cylindrical shape. The valve body 150A is housed within the housing recess portion 141 provided in the plunger 140 as mentioned above, and as a result is disposed opposite from the outflow port 132 provided in the core 130.

Here, the valve body 150A is positioned so that a part thereof protrudes toward the core 130 beyond the axial direction end surface 143 of the plunger 140 that opposes the core 130. Note that the valve body 150A is affixed to the plunger 140 using an adhesive or the like, for example.

The spring 160 is interposed between the core 130 and the plunger 140 on the inside of the bobbin 120. The spring 160 biases the plunger 140 in the direction away from the core 130.

FIGS. 4 through 6 are enlarged cross-sectional views of primary components, illustrating operations of the flow control valve according to the present embodiment. Here, FIG. 4 illustrates the flow control valve in an open state, FIG. 5 illustrates the flow control valve in a closed state, and FIG. 6 illustrates the flow control valve in a limited flow state. Next, operations of the flow control valve 100A according to the present embodiment will be described with reference to FIGS. 4 through 6. Note that the following describes a distance between the core 130 and the plunger 140 (in other words, a distance between the axial direction end surface 133 of the core 130 and the axial direction end surface 143 of the plunger 140 in the axial direction of the flow control valve 100A) as L.

As shown in FIG. 4, when the flow control valve 100A is not operating, the solenoid coil 121 is not electrified and is in a non-electrified state, and thus a magnetic circuit is not formed. Accordingly, the plunger 140 is not pulled toward the core 130, and, due to the biasing force of the spring 160, is located at a position distanced from the core 130 in the axial direction of the flow control valve 100A by a predetermined distance L1. If the position of the valve body 150A at that time is taken as a first position, the first position is a position in which the valve body 150A is distanced from the outflow port 132 by a predetermined distance.

In this state, the outflow port 132 is not blocked by the valve body 150A, and is in a fully open state. Accordingly, compressed air present within the pressurizing air bladder 42 that communicates with the nozzle portion 131 is exhausted via the outflow port 132 to a space located between the core 130 and the plunger 140, and is furthermore exhausted to the exterior of the flow control valve 100A via a gap between the bobbin 120 and the plunger 140.

As shown in FIGS. 5 and 6, when the flow control valve 100A is operating, the solenoid coil 121 is electrified and is thus in an electrified state; as a result, a magnetic circuit is formed, with a magnetic flux passing through the frame 110, the core 130, the plunger 140, and the base 111. Accordingly, the plunger 140 is pulled toward the core 130 in the axial direction of the flow control valve 100A, against the biasing force of the spring 160.

As shown in FIG. 5, in the case where the current applied to the solenoid coil 121 is greater than or equal to a predetermined value, the plunger 140 is pulled to a maximum extent toward the core 130 in the axial direction, causing the valve body 150A to come into contact with the core 130; as a result, the outflow port 132 is completely blocked by the valve body 150A and is thus completely closed. In this state, the compressed air is completely prevented from flowing out via the outflow port 132, and thus the internal pressure in the pressurizing air bladder 42 is maintained. Note that the position of the valve body 150A at this time is a second position.

The flow control valve 100A according to the present embodiment is configured so that when the valve body 150A is in the second position and completely blocks the outflow port 132, the plunger 140 is not in contact with the core 130; as a result, in this state, the plunger 140 is located in a position distanced from the core 130 in the axial direction of the flow control valve 100A by a predetermined distance L2. This is mainly due to part of the valve body 150A being provided so as to protrude toward the core 130 beyond the axial direction end surface 143 of the plunger 140 as described above. By employing such a configuration, the flow rate in the limited flow state, which will be described later, can be precisely controlled; the reasons for this will be described in detail later.

Meanwhile, as shown in FIG. 6, in the case where the current applied to the solenoid coil 121 is less than the predetermined value, the plunger 140 is pulled to a certain extent toward the core 130 in the axial direction; the distance L between the core 130 and the plunger 140 takes on a value that is lower than the aforementioned distance L1 and greater than the aforementioned distance L2. Accordingly, the valve body 150A is disposed in a third position, between the aforementioned first position and second position.

In this state, the valve body 150A does not completely block the outflow port 132, but the distance therebetween has decreased and thus the outflow port 132 is blocked to a certain extent. Accordingly, although the compressed air does flow out via the outflow port 132, the compressed air is prevented by the valve body 150A from flowing out from the outflow port 132 to a certain extent, and the outflow rate is thus limited.

Here, a distance between an open face of the outflow port 132 and a primary surface of the valve body 150A located on the side toward the outflow port 132 is determined by the distance L between the core 130 and the plunger 140, and the distance L is adjusted in a variable manner by controlling the magnitude of the current applied to the solenoid coil 121. Accordingly, by adjusting the driving voltage of the flow control valve 100A in order to adjust the distance L, the flow rate of the compressed air flowing out from the outflow port 132 can be adjusted in a variable manner.

Next, a plunger driving force required for the valve body 150A to completely close the outflow port 132 will be described with reference to FIG. 5, based on specifications of a standard blood pressure monitor.

Referring to FIG. 5, it is necessary for the thrust F0 [N] required to completely close the outflow port 132 using the valve body 150A against the internal pressure of the pressurizing air bladder 42 (the cuff pressure, in other words) to be of a magnitude greater than or equal to a resistance Fa [N] that is the total sum of a reaction force F1 [N] against a cuff pressure P [mmHg] and a reaction force F2 [N] that is the sum of the deformation reactive force of the valve body 150A configured of an elastic member pressed against the periphery of the outflow port 132 and the deformation reactive force of the spring 160 serving as the biasing member that undergoes compressive deformation. Accordingly, when an inner diameter of the outflow port 132 is represented by $\varphi$ [cm], the following Formulas (1) to (3) hold true.

$$Fa = F1 + F2 \quad (1)$$

$$F0 > Fa \quad (2)$$

$$F1 = P \times 1.333 \times 10^{-2} \times \pi \times \varphi^2/4 \quad (3)$$

Based on the specifications of a standard blood pressure monitor, when a maximum cuff pressure P is set to 300 [mmHg] and the inner diameter $\varphi$ of the outflow port 132 is set to 0.16 [cm], for example, the aforementioned reactive force F1 is $8.04 \times 10^{-2}$ [N], based on the aforementioned Formula (3).

Furthermore, assuming the aforementioned reactive force F2 is $3.8 \times 10^{-2}$ [N] based on the standard material characteristics of the valve body 150A and the spring 160, the aforementioned resistance Fa is $1.18 \times 10^{-1}$ [N]=12.0 [g], based on the aforementioned Formula (1).

As a result, based on the aforementioned Formula (2), a force of greater than or equal to $1.5 \times 10^{-1}$ and approximately $2.0 \times 10^{-1}$ [N] is required for the aforementioned thrust F0, and thus any driving force for the plunger 140 capable of realizing this thrust F0 may be employed.

Here, a driving force Fb [N] of the plunger 140 is expressed by the following Formula (4), using a magnetic flux density B [T], a current I [A] applied to the solenoid coil 121, and a useful coil length Lc [m] of the solenoid coil 121.

$$Fb = B \times I \times Lc \quad (4)$$

Accordingly, by adjusting the current I [A] applied to the solenoid coil 121 and the useful coil length Lc [m] of the solenoid coil 121 as appropriate, the driving force Fb [N] of the plunger 140 can be set to a desired value, and the aforementioned thrust F0 can be fully realized.

Note that changing the driving voltage, changing the wire diameter of the coiled wire, and so on can be given as methods for adjusting the current I [A] applied to the solenoid coil 121. Meanwhile, changing the number of winds in the coiled wire and so on can be given as a method for adjusting the useful coil length Lc [m] of the solenoid coil 121. Accordingly, changing the resistance value of the solenoid coil 121 and adjusting the driving voltage as appropriate are effective for realizing the aforementioned thrust F0 in a precise manner.

As described above, the flow control valve 100A according to the present embodiment is configured so that the plunger 140 is not in contact with the core 130 in the state where the valve body 150A is in the second position, which completely blocks the outflow port 132 (that is, the closed state; see FIG. 5). By employing such configuration, in the aforementioned limited flow state (see FIG. 6), the driving force of the plunger 140 can be increased/reduced as necessary with ease by adjusting the driving voltage and in turn adjusting the magnitude of the current applied to the solenoid coil 121; as a result, precise flow rate control can be carried out. The reason for this will be described in detail hereinafter based on results of a verification test carried out using an actual trial piece.

In the verification tests, the flow control valve 100A according to the present embodiment as described above was created as a working example, a flow control valve 100X (see FIGS. 8 and 9) used in conventional blood pressure monitors was prepared as a conventional example, and the relationship between the core-plunger distance and the plunger driving force was actually measured using these examples.

Figure 7:
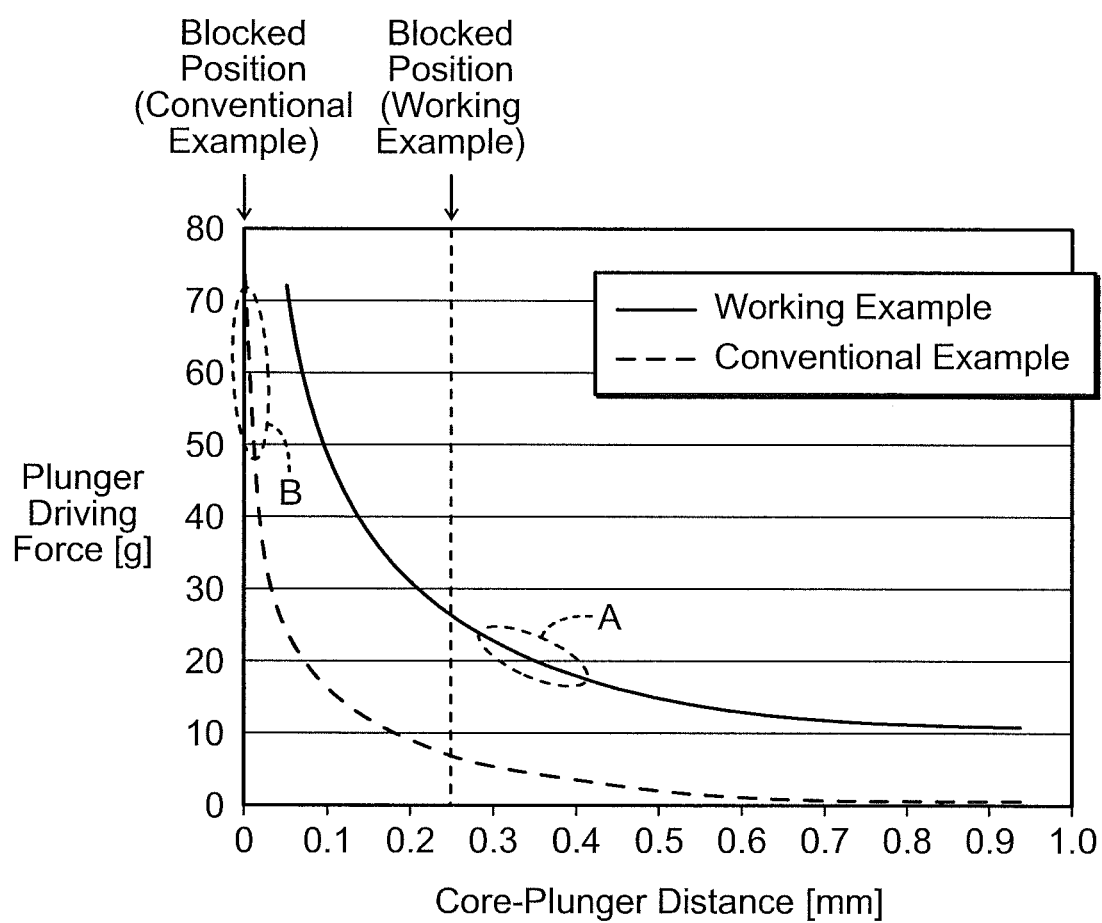
FIG. 7 is a graph illustrating a relationship between a core-plunger distance and a plunger driving force in flow control valves according to a working example and a conventional example, respectively.
Figure 8:
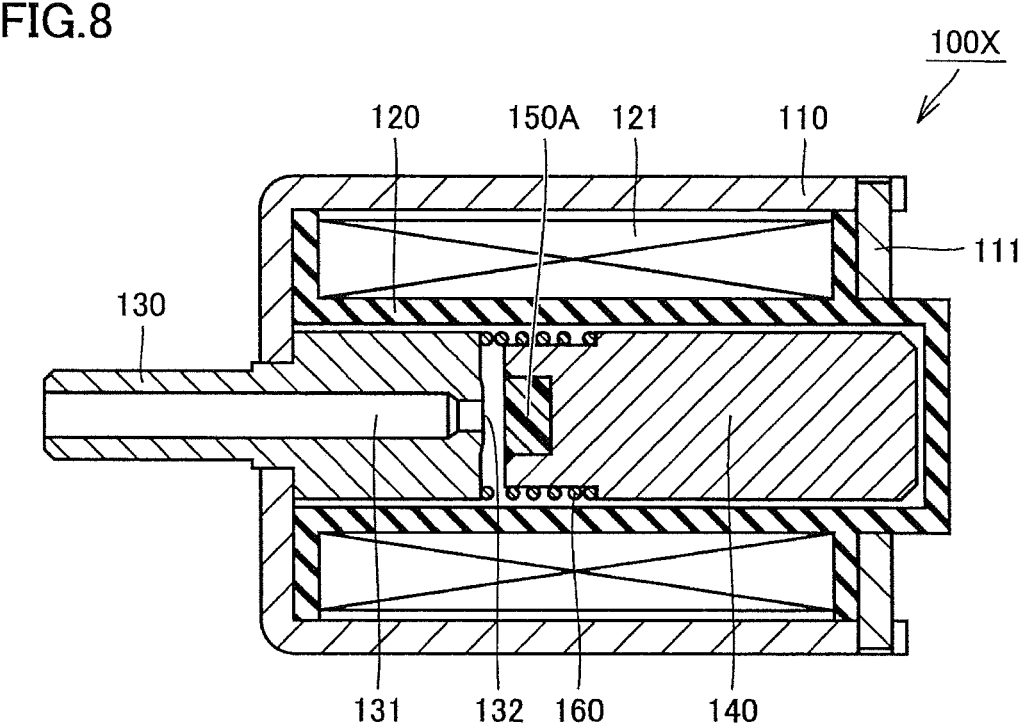
FIG. 8 is a schematic cross-sectional view of the flow control valve according to the conventional example.
Figure 9:
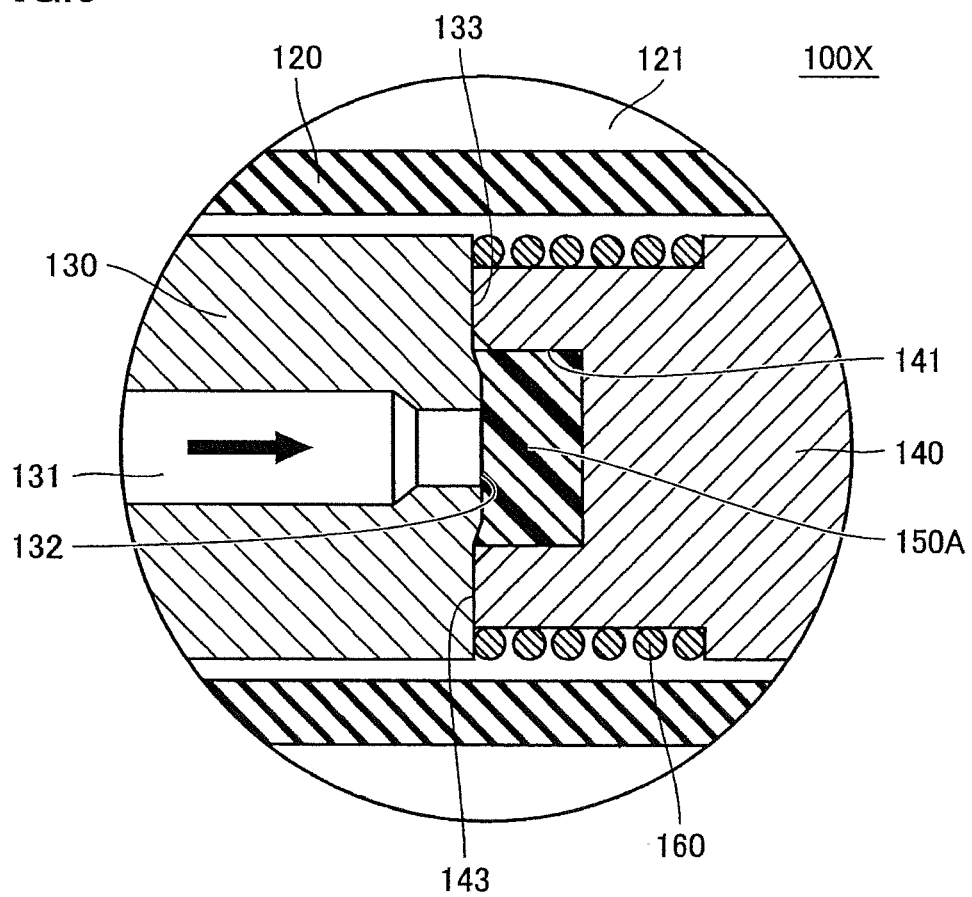
FIG. 9 is an enlarged cross-sectional view of primary components, illustrating the flow control valve shown in FIG. 8 in a closed state.

FIG. 7 is a graph illustrating the relationship between a core-plunger distance and the plunger driving force in the flow control valves according to the working example and the conventional example, respectively. FIG. 8, meanwhile, is a schematic cross-sectional view of the flow control valve according to the conventional example, whereas FIG. 9 is an enlarged cross-sectional view of primary components, illustrating the flow control valve shown in FIG. 8 in a closed state.

As shown in FIG. 8, when compared to the flow control valve according to the working example (the flow control valve 100A according to the present embodiment), the flow control valve 100X according to the conventional example is different in that the valve body 150A that is incorporated into the plunger 140 is completely contained within the housing recess portion 141 provided in the plunger 140, and there is no portion that protrudes toward the core 130 beyond the main surface of the plunger 140 that opposes the core 130. Accordingly, as shown in FIG. 9, when the plunger 140 is pulled to the maximum limit toward the core 130 in the axial direction, the outflow port 132 is completely blocked and closed by the valve body 150A as a result of the valve body 150A making contact with the core 130, and the plunger 140 makes contact with and is affixed to the core 130.

Meanwhile, the flow control valve according to the working example differs from the flow control valve 100X according to the conventional example in that the driving voltage, resistance value of the solenoid coil, and spring constant of the spring serving as a biasing member are optimized based on the specifications of the blood pressure monitor in which those elements are provided.

As shown in FIG. 7, in the flow control valve 100X according to the conventional example, there is a distance generally near 0 [mm] between the core and the plunger in the limited flow state, in the case where a blocked position, in which the outflow port is blocked by the valve body, is a position where the core and the plunger are in contact with each other, and actual flow rate control thereof is difficult but is assumed to be possible. Accordingly, when the magnitude of the current applied to the solenoid coil is changed by adjusting the driving voltage in that range (the range indicated by the letter B in FIG. 7), the plunger driving force that is obtained will be high; however, the plunger driving force will also increase/decrease dramatically, which is understood as making it impossible, in actuality, to carry out precise flow rate control.

On the other hand, in the flow control valve according to the working example, the blocked position in which the outflow port is blocked by the valve body is set to a position where the distance between the core and the plunger is in the vicinity of 0.25 [mm]. The distance between the core and the plunger in the aforementioned limited flow state (during flow rate control) is a small range from approximately 0.3 [mm] to 0.4 [mm]. Accordingly, when the magnitude of the current applied to the solenoid coil is changed by adjusting the driving voltage within this range, the plunger driving force will increase/decrease appropriately, and because the driving voltage and the resistance value of the solenoid coil are optimized, the driving force itself also has a sufficient magnitude, which is understood as making it possible to realize precise flow rate control.

By controlling the flow rate using a range (indicated by the letter A in FIG. 7) in which the correlation relationship between the core-plunger distance and the plunger driving force appearing in the graph in FIG. 7 is comparatively level in this manner, precise flow rate control can be carried out.

Although the aforementioned blocked position is set to an optimal size as suited to the specifications of the blood pressure monitor 1, according to one or more embodiments of the present invention, in the case where the specifications of a typical blood pressure monitor are to be taken into consideration, the size is greater than or equal to 0.2 mm so that drastic changes in the driving force do not occur. Furthermore, during flow rate control, according to one or more embodiments of the claimed invention, the flow rate control is set to be carried out from a position further distanced from the blocked position by a predetermined distance.

In this manner, by employing the flow control valve 100A according to the present embodiment, the driving force of the plunger 140 increases/decreases as appropriate by adjusting the driving voltage and changing the magnitude of the current applied to the solenoid coil 121, and the driving force itself is of a sufficient magnitude; this makes it possible to carry out precise flow rate control, which has been difficult conventionally.

Figure 10:
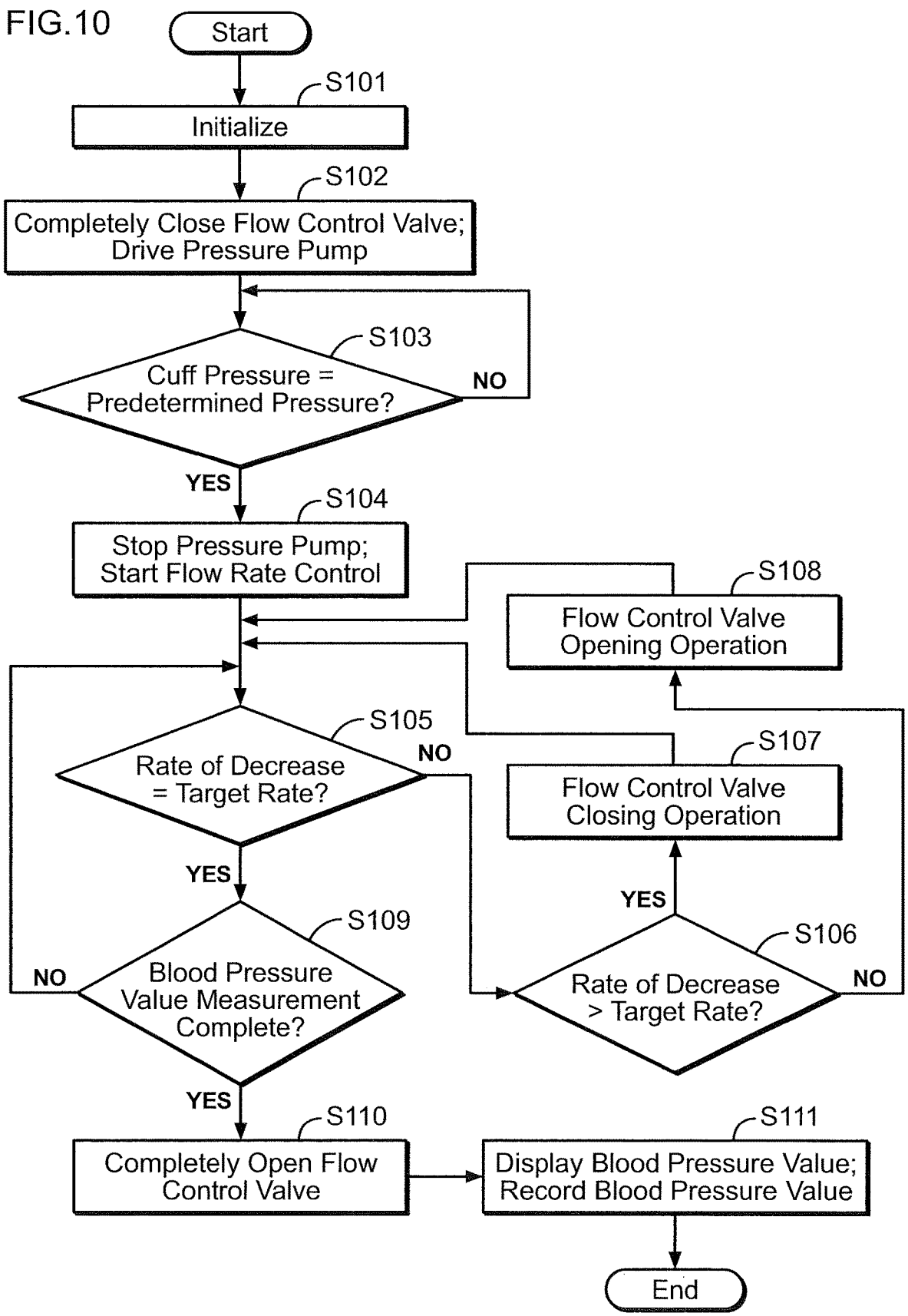
FIG. 10 is a diagram illustrating an operational flow based on a deflation measurement method in the blood pressure monitor according to the first embodiment of the present invention.
Figure 14:
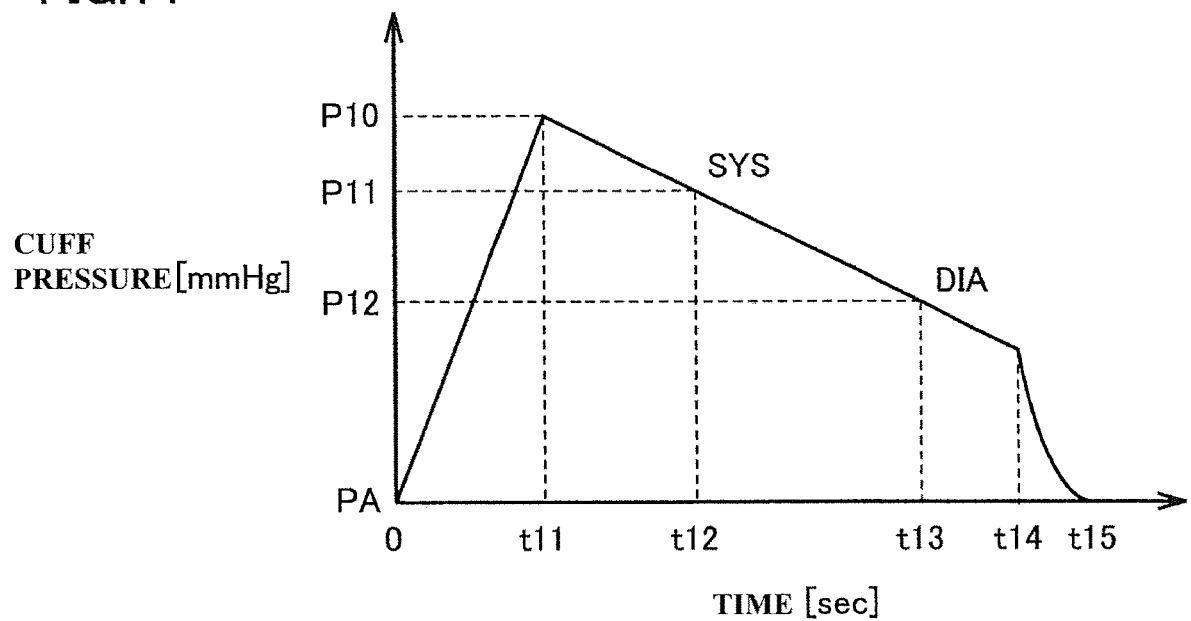
FIG. 14 is a graph illustrating changes over time in the internal pressure of a pressurizing air bladder, in the case where the operational flow shown in FIG. 10 is carried out by the blood pressure monitor according to the first embodiment of the present invention.

FIG. 10 is a diagram illustrating an operational flow based on a deflation measurement method in the blood pressure monitor according to the present embodiment, and FIGS. 11 to 13 are diagrams respectively illustrating specific operations of the blood pressure monitor during rapid inflation, slow deflation, and rapid deflation in the case of the operational flow shown in FIG. 10. FIG. 14, meanwhile, is a graph illustrating changes over time in the internal pressure of the pressurizing air bladder, in the case where the operational flow shown in FIG. 10 is carried out. Next, specific operations of the blood pressure monitor 1 and so on in the case where the blood pressure monitor 1 according to the present embodiment measures a blood pressure value based on the deflation measurement method will be described with reference to FIGS. 10 to 14. A program corresponding to the flowchart shown in FIG. 10 is stored in the memory unit 22 in advance, and those processes are executed by the control unit 20 reading out the program from the memory unit 22 and executing the program.

When measuring a blood pressure value based on the deflation measurement method, the measurement subject first wraps and secures the cuff 40 around his or her upper arm, and then turns the blood pressure monitor 1 on by operating the operating unit 23 provided in the main body 10. As a result, electricity is supplied from the power source unit 24 to the control unit 20, thus driving the control unit 20. As shown in FIG. 10, the control unit 20 first initializes the blood pressure monitor 1 after the stated driving (step S101).

Next, as shown in FIG. 10, the control unit 20 stands by for an instruction to start the measurement from the measurement subject, and in the case where an instruction to start the measurement has been supplied as a result of the measurement subject operating the operating unit 23, the flow control valve 100A is closed completely and the pressure pump 31 is driven, raising the cuff pressure in the pressurizing air bladder 42 as a result (step S102).

Specifically, as shown in FIG. 11, the control unit 20 drives the pressure pump 31 by supplying a predetermined control signal to the pressure pump driving circuit 34, whereupon compressed air is supplied from the pressure pump 31 to the pressurizing air bladder 42; the control unit 20 also drives the flow control valve 100A by supplying a predetermined control signal to the flow control valve driving circuit 35, and the outflow port 132 is completely closed by the valve body 150A. The driving voltage applied to the flow control valve 100A at this time is a voltage of a magnitude at which the outflow port 132 can be completely closed by the valve body 150A.

Step S102 corresponds to a rapid inflation process that inflates the pressurizing air bladder 42 at a comparatively high rate of increase. In other words, as shown in FIG. 14, during the rapid inflation process, the cuff pressure increases according to a predetermined rate of increase (see time 0 to t11), and the pressurizing air bladder 42 expands as a result, compressing the upper arm of the measurement subject.

Next, as shown in FIG. 10, the control unit 20 determines whether or not the cuff pressure has reached a predetermined pressure (step S103). In the case where the control unit 20 determines that the cuff pressure has not reached the predetermined pressure (the case of NO in step S103), the control unit 20 continues driving the pressure pump 31, whereas in the case where the control unit 20 determines that the cuff pressure has reached the predetermined pressure (the case of YES in step S103), the control unit 20 stops the pressure pump 31 and starts flow rate control for exhausting the compressed air using the flow control valve 100A (step S104). Here, the stated predetermined pressure is a pressure that is greater than a typical systolic blood pressure value, as indicated by a cuff pressure P10 shown in FIG. 14 (the cuff pressure at time t11).

Specifically, as shown in FIG. 12, the control unit 20 stops the pressure pump 31 by supplying a predetermined control signal to the pressure pump driving circuit 34, and continues to drive the flow control valve 100A at reduced output by supplying a predetermined control signal to the flow control valve driving circuit 35; this moves the valve body 150A and opens the outflow port 132 slightly. As a result, the compressed air present within the pressurizing air bladder 42 is gradually exhausted via the flow control valve 100A. The driving voltage applied to the flow control valve 100A at this time is a voltage of a magnitude that is lower than the voltage at which the outflow port 132 can be completely closed by the valve body 150A, and is a voltage within a range in which the flow rate of the compressed air flowing from the outflow port 132 can be limited to a predetermined flow rate.

The flow rate control for exhausting the compressed air is carried out based on changes in the cuff pressure detected by the pressure sensor 33.

To be more specific, as shown in FIG. 10, the control unit 20 determines, based on changes in the cuff pressure detected by the pressure sensor 33, whether or not a rate of decrease in the cuff pressure matches a predetermined target rate (step S105). In the case where the control unit 20 determines that the rate of decrease in the cuff pressure does not match the predetermined target rate (the case of NO in step S105), the control unit 20 determines whether or not the rate of decrease is greater than the target rate (step S106). In the case where the control unit 20 determines that the rate of decrease is greater than the target rate (the case of YES in step S106), the control unit 20 slightly raises the driving voltage for the flow control valve 100A so as to move the valve body 150A in a closing direction and slow the rate of decrease (step S107), whereas in the case where the control unit 20 determines that the rate of decrease is lower than the target rate (the case of NO in step S106), the control unit 20 slightly lowers the driving voltage for the flow control valve 100A so as to move the valve body 150A in an opening direction and raise the rate of decrease (step S108); thereafter, in either case, the flow rate control for exhausting the compressed air is continued (the process returns to step S105).

Meanwhile, in the case where the control unit 20 determines that the rate of decrease in the cuff pressure matches the predetermined target rate (the case of YES in step S105), the control unit 20 determines whether or not the blood pressure value measurement has ended (step S109); in the case where the control unit 20 determines that the blood pressure value measurement has not ended (the case of NO in step S109), the flow rate control for exhausting the compressed air is continued (the process returns to step S105). According to one or more embodiments of the present invention, a predetermined constant rate of decrease is employed as the aforementioned target rate.

Steps S105 to S109 correspond to a slow deflation process that gradually deflates the pressurizing air bladder 42. In other words, as shown in FIG. 14, in the slow deflation process, the cuff pressure is gradually reduced in accordance with a predetermined target rate (see time t11 to time t14), and the pressurizing air bladder 42 gradually contracts as a result.

During the slow deflation process, the control unit 20 calculates the blood pressure value using a known procedure. Specifically, the control unit 20 extracts pulse wave information based on an oscillation frequency obtained from the oscillation circuit 36, and calculates the systolic blood pressure value and the diastolic blood pressure value based on the extracted pulse wave information. Through this, as shown in FIG. 14, the systolic blood pressure value (SYS) is first calculated as a cuff pressure P11 at time t12, after which the diastolic blood pressure value (DIA) is calculated as a cuff pressure P12 at time t13.

As shown in FIG. 10, in the case where the control unit 20 determines that the blood pressure value measurement has ended (the case of YES in step S109), the compressed air is rapidly exhausted by completely opening the flow control valve 100A, which causes the cuff pressure to drop (step S110).

Specifically, as shown in FIG. 13, the control unit 20 stops the flow control valve 100A by supplying a predetermined control signal to the flow control valve driving circuit 35; this moves the valve body 150A and places the outflow port 132 in a completely open state. As a result, the compressed air present within the pressurizing air bladder 42 is rapidly exhausted via the flow control valve 100A.

Step S110 corresponds to a rapid deflation process that deflates the pressurizing air bladder 42 rapidly. In other words, as shown in FIG. 14, in the rapid deflation process, the cuff pressure drops to atmospheric pressure PA rapidly at a predetermined rate of decrease (see time t14 to time t15); the pressurizing air bladder 42 contracts completely as a result, removing the pressure from the upper arm of the measurement subject.

Next, as shown in FIG. 10, the control unit 20 displays the blood pressure value in the display unit 21 as a measurement result, and stores that blood pressure value in the memory unit 22 (step S111). The control unit 20 then stands by for a power off command from the measurement subject, and ends the operations.

Figure 15:
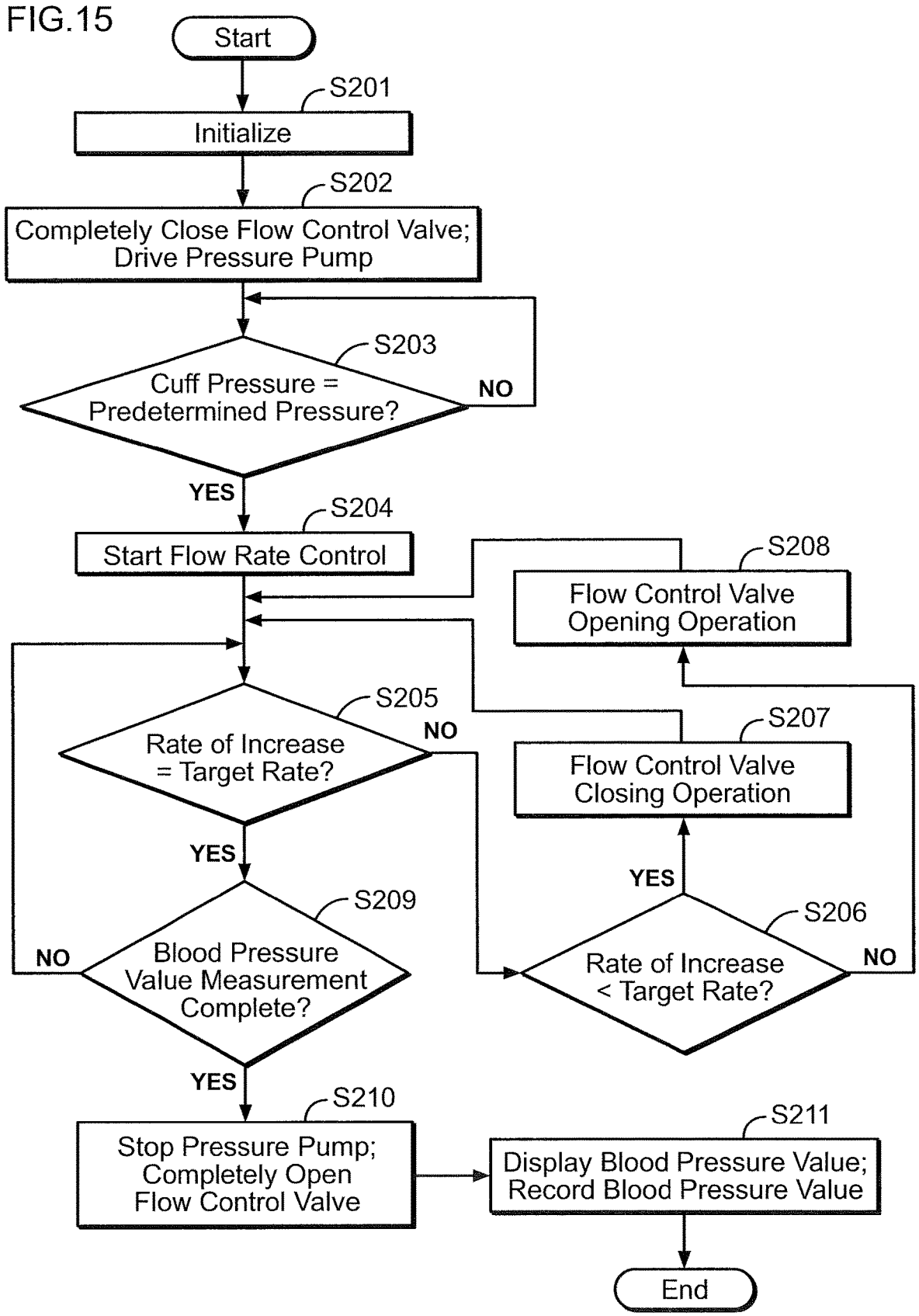
FIG. 15 is a diagram illustrating an operational flow based on an inflation measurement method in the blood pressure monitor according to the first embodiment of the present invention.
Figure 16:
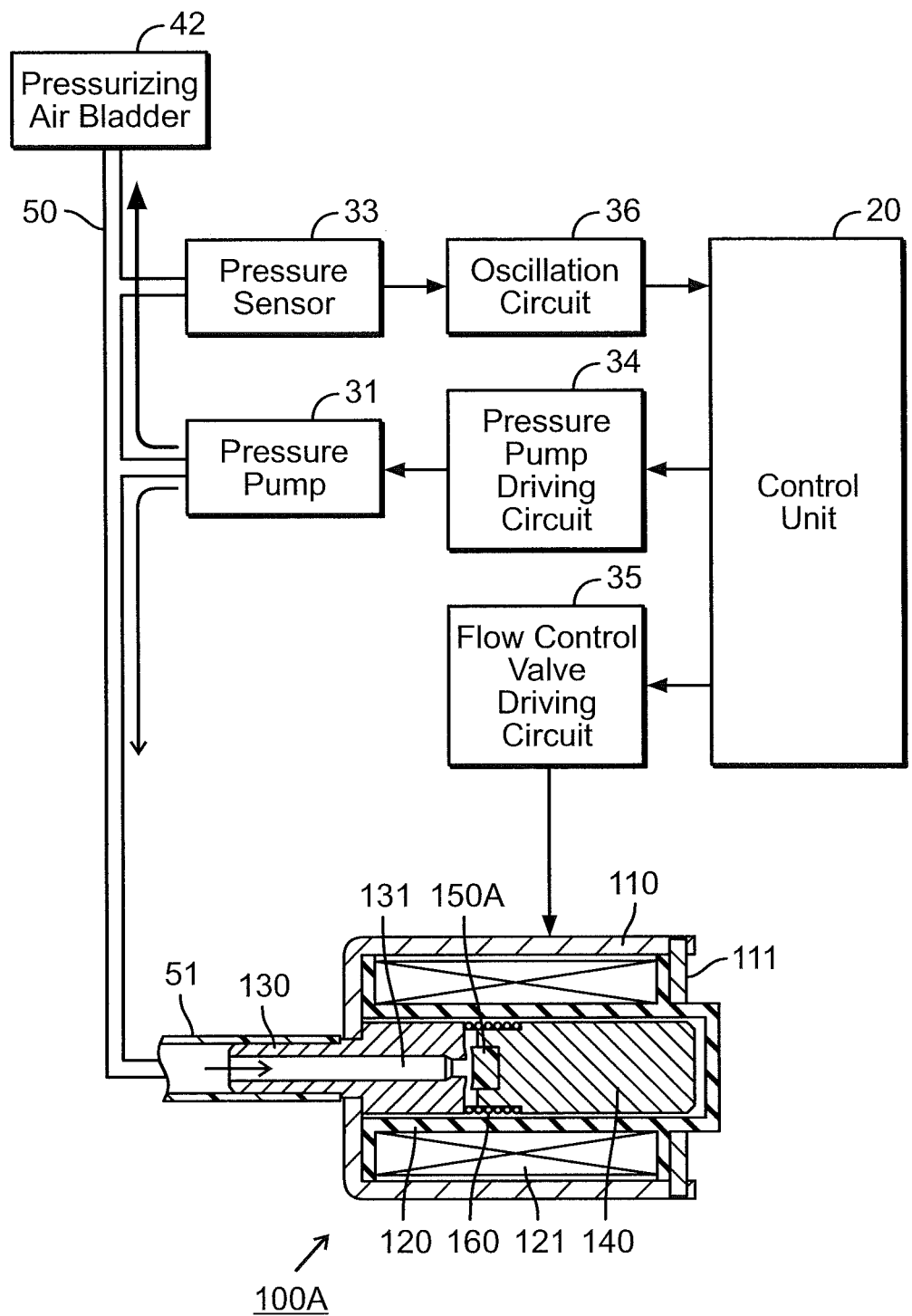
FIG. 16 is a diagram illustrating specific operations performed during slow inflation, in the case where the operational flow shown in FIG. 15 is carried out by the blood pressure monitor according to the first embodiment of the present invention.
Figure 17:
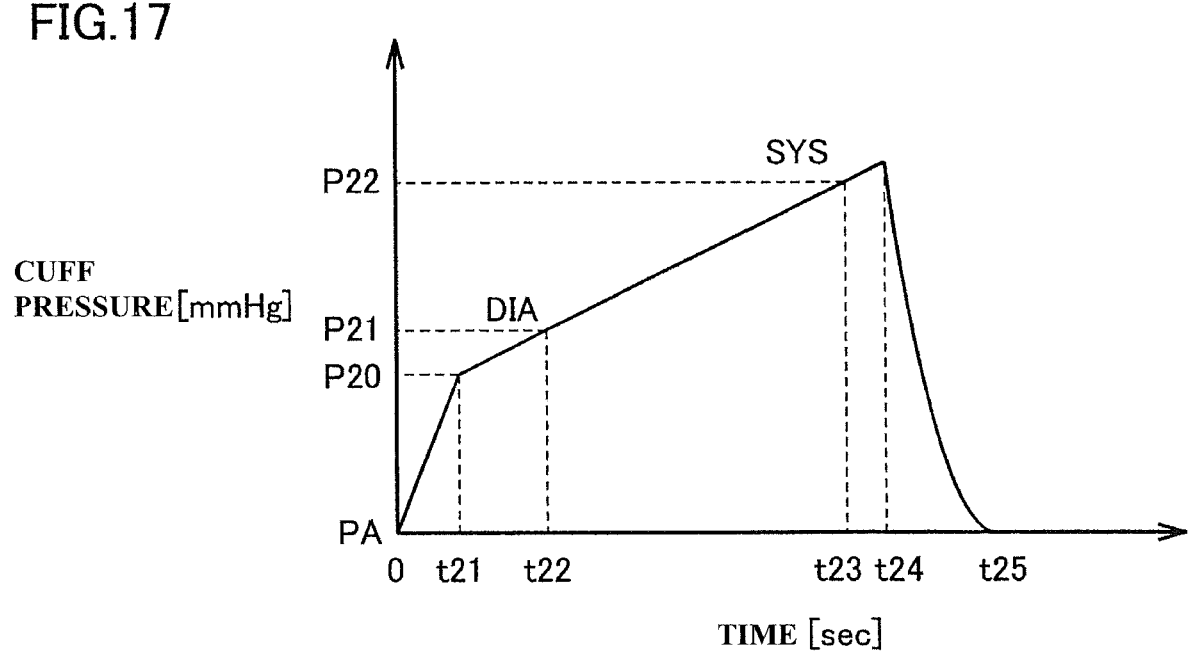
FIG. 17 is a graph illustrating changes over time in the internal pressure of a pressurizing air bladder, in the case where the operational flow shown in FIG. 15 is carried out by the blood pressure monitor according to the first embodiment of the present invention.

FIG. 15 is a diagram illustrating an operational flow based on an inflation measurement method in the blood pressure monitor according to the present embodiment, and FIG. 16 is a diagram illustrating specific operations performed by the blood pressure monitor during slow inflation, in the case where the operational flow shown in FIG. 15 is carried out. FIG. 17, meanwhile, is a graph illustrating changes over time in the internal pressure of the pressurizing air bladder, in the case where the operational flow shown in FIG. 15 is carried out. Next, specific operations of the blood pressure monitor 1 and so on in the case where the blood pressure monitor 1 according to the present embodiment measures a blood pressure value based on the inflation measurement method will be described with reference to FIGS. 15 to 17. A program corresponding to the flowchart shown in FIG. 15 is stored in the memory unit 22 in advance, and those processes are executed by the control unit 20 reading out the program from the memory unit 22 and executing the program.

When measuring a blood pressure value based on the inflation measurement method, the measurement subject first wraps and secures the cuff 40 around his or her upper arm, and then turns the blood pressure monitor 1 on by operating the operating unit 23 provided in the main body 10. As a result, electricity is supplied from the power source unit 24 to the control unit 20, thus driving the control unit 20. As shown in FIG. 15, the control unit 20 first initializes the blood pressure monitor 1 after the stated driving (step S201).

Next, as shown in FIG. 15, the control unit 20 stands by for an instruction to start the measurement from the measurement subject, and in the case where an instruction to start the measurement has been supplied as a result of the measurement subject operating the operating unit 23, the flow control valve 100A is closed completely and the pressure pump 31 is driven, raising the cuff pressure in the pressurizing air bladder 42 as a result (step S202). The specific operations of the blood pressure monitor 1 at this time are the same as the operations indicated in FIG. 11 and described above, and thus descriptions thereof will not be repeated here.

Step S202 corresponds to a rapid inflation process that inflates the pressurizing air bladder 42 at a comparatively high rate of increase. In other words, as shown in FIG. 17, during the rapid inflation process, the cuff pressure increases according to a predetermined rate of increase (see time 0 to t21), and the pressurizing air bladder 42 expands as a result, compressing the upper arm of the measurement subject.

Next, as shown in FIG. 15, the control unit 20 determines whether or not the cuff pressure has reached a predetermined pressure (step S203). In the case where the control unit 20 determines that the cuff pressure has not reached a predetermined pressure (the case of NO in step S203), the control unit 20 continues to drive the pressure pump 31, whereas in the case where the control unit 20 determines that the cuff pressure has reached a predetermined pressure (the case of YES in step S203), the control unit 20 starts flow rate control for exhausting the compressed air using the flow control valve 100A (step S204). Here, the stated predetermined pressure is a pressure that is lower than a typical diastolic blood pressure value, as indicated by a cuff pressure P20 shown in FIG. 17 (the cuff pressure at time t21).

Specifically, as shown in FIG. 16, the control unit 20 continues to drive the flow control valve 100A at reduced output by supplying a predetermined control signal to the flow control valve driving circuit 35; this moves the valve body 150A and opens the outflow port 132 slightly. As a result, some of the compressed air sent from the pressure pump 31 to the pressurizing air bladder 42 is exhausted via the flow control valve 100A. The driving voltage applied to the flow control valve 100A at this time is a voltage of a magnitude that is lower than the voltage at which the outflow port 132 can be completely closed by the valve body 150A, and is a voltage within a range in which the flow rate of the compressed air flowing from the outflow port 132 can be limited to a predetermined flow rate.

The flow rate control for exhausting the compressed air is carried out based on changes in the cuff pressure detected by the pressure sensor 33.

To be more specific, as shown in FIG. 15, the control unit 20 determines, based on changes in the cuff pressure detected by the pressure sensor 33, whether or not a rate of increase in the cuff pressure matches a predetermined target rate (step S205). In the case where the control unit 20 determines that the rate of increase in the cuff pressure does not match the predetermined target rate (the case of NO in step S205), the control unit 20 determines whether or not the rate of increase is lower than the target rate (step S206). In the case where the control unit 20 determines that the rate of increase is lower than the target rate (the case of YES in step S206), the control unit 20 slightly raises the driving voltage for the flow control valve 100A so as to move the valve body 150A in the closing direction and raise the rate of increase (step S207), whereas in the case where the control unit 20 determines that the rate of increase is higher than the target rate (the case of NO in step S206), the control unit 20 slightly lowers the driving voltage for the flow control valve 100A so as to move the valve body 150A in the opening direction and lower the rate of increase (step S208); thereafter, in either case, the flow rate control for exhausting the compressed air is continued (the process returns to step S205).

Meanwhile, in the case where the control unit 20 determines that the rate of increase in the cuff pressure matches the predetermined target rate (the case of YES in step S205), the control unit 20 determines whether or not the blood pressure value measurement has ended (step S209); in the case where the control unit 20 determines that the blood pressure value measurement has not ended (the case of NO in step S209), the flow rate control for exhausting the compressed air is continued (the process returns to step S205). According to one or more embodiments of the present invention, a predetermined constant rate of increase is employed as the aforementioned target rate.

Steps S205 to S209 correspond to a slow inflation process that gradually inflates the pressurizing air bladder 42. In other words, as shown in FIG. 17, in the slow inflation process, the cuff pressure is gradually increased in accordance with a predetermined target rate (see time t21 to time t24), and the pressurizing air bladder 42 gradually expands as a result.

During the slow inflation process, the control unit 20 calculates the blood pressure value using a known procedure. Specifically, the control unit 20 extracts pulse wave information based on an oscillation frequency obtained from the oscillation circuit 36, and calculates the systolic blood pressure value and the diastolic blood pressure value based on the extracted pulse wave information. Through this, as shown in FIG. 17, the diastolic blood pressure value (DIA) is first calculated as a cuff pressure P21 at time t22, after which the systolic blood pressure value (SYS) is calculated as a cuff pressure P22 at time t23.

As shown in FIG. 15, in the case where the control unit 20 determines that the blood pressure value measurement has ended (the case of YES in step S209), the compressed air is rapidly exhausted by stopping the pressure pump 31 and completely opening the flow control valve 100A, which causes the cuff pressure to drop (step S210). The specific operations of the blood pressure monitor 1 at this time are the same as the operations indicated in FIG. 13 and described above, and thus descriptions thereof will not be repeated here.

Step S210 corresponds to a rapid deflation process that deflates the pressurizing air bladder 42 rapidly. In other words, as shown in FIG. 17, in the rapid deflation process, the cuff pressure drops to atmospheric pressure PA rapidly at a predetermined rate of decrease (see time t24 to time t25); the pressurizing air bladder 42 contracts completely as a result, removing the pressure from the upper arm of the measurement subject.

Next, as shown in FIG. 15, the control unit 20 displays the blood pressure value in the display unit 21 as a measurement result, and stores that blood pressure value in the memory unit 22 (step S211). The control unit 20 then stands by for a power off command from the measurement subject, and ends the operations.

By employing the blood pressure monitor 1 according to the present embodiment as described thus far, the flow control valve 100A according to the present embodiment as described above is employed as the exhaust valve, making it possible to precisely control the internal pressure of the pressurizing air bladder 42; furthermore, it is not necessary to provide a separate flow control mechanism, which makes it possible to realize a simple configuration.

First Variation

Figure 18:
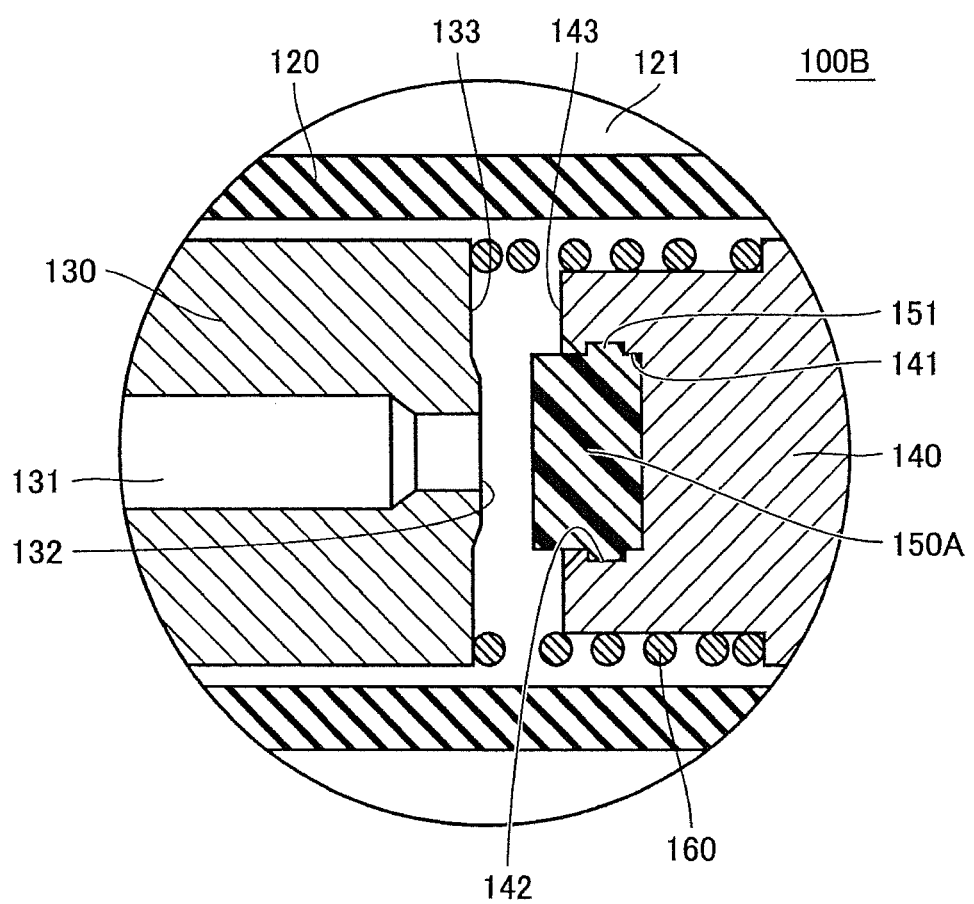
FIG. 18 is an enlarged cross-sectional view of primary components of a flow control valve according to a first variation on the first embodiment of the present invention.

FIG. 18 is an enlarged cross-sectional view of primary components of a flow control valve according to a first variation on the present embodiment. A flow control valve 100B according to the first variation on the present embodiment will be described next with reference to FIG. 18.

As shown in FIG. 18, the flow control valve 100B according to the first variation differs from the flow control valve 100A according to the aforementioned present embodiment in terms of the structure for incorporating the valve body 150A into the plunger 140. Specifically, the flow control valve 100B according to the first variation is configured with an engagement recess portion 142 being provided in the inner circumferential surface of the housing recess portion 141 provided in the plunger 140 and an engagement protruding portion 151 being provided in the outer circumferential surface of the valve body 150A; when the valve body 150A is press-fitted into the housing recess portion 141, the engagement protruding portion 151 engages with the engagement recess portion 142, thus incorporating the valve body 150A into the plunger 140.

By employing such a configuration, it is no longer necessary to use an adhesive when incorporating the valve body 150A into the plunger 140, which provides effects of simplifying the incorporating process and enabling a reduction in manufacturing costs, in addition to the effects described in the present embodiment above.

Second Variation

Figure 19:
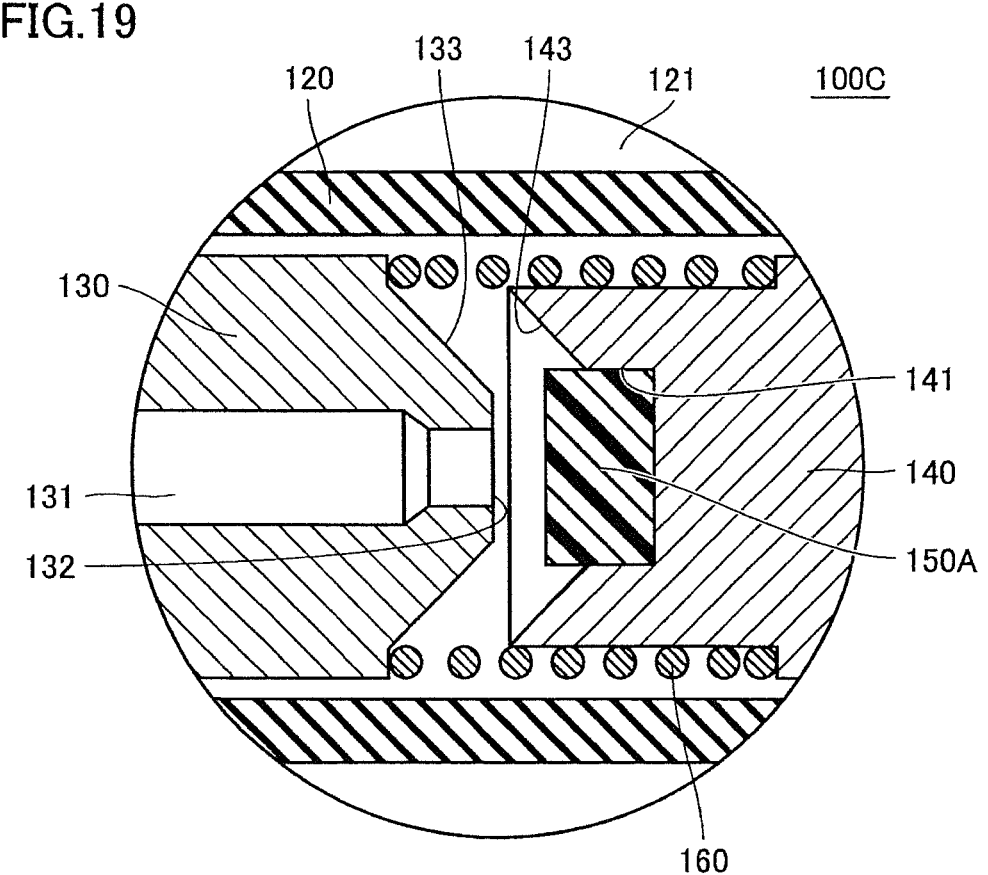
FIG. 19 is an enlarged cross-sectional view of primary components of a flow control valve according to a second variation on the first embodiment of the present invention.

FIG. 19 is an enlarged cross-sectional view of primary components of a flow control valve according to a second variation on the present embodiment. A flow control valve 100C according to the second variation on the present embodiment will be described next with reference to FIG. 19.

As shown in FIG. 19, the flow control valve 100C according to the second variation differs from the flow control valve 100A according to the aforementioned present embodiment in terms of the shapes of the axial direction end surface 133 of the core 130 and the axial direction end surface 143 of the plunger 140. Specifically, in the flow control valve 100C according to the second variation, the axial direction end surface 143 of the plunger 140 has a conical recessed shape, whereas the axial direction end surface 133 of the core 130 has a conical protruding shape.

By employing such a configuration, not only can the effects described above in the present embodiment be obtained, but the surface area between the axial direction end surface 133 of the core 130 and the axial direction end surface 143 of the plunger 140, which is a region through which a magnetic flux flows during electrification, can also be increased, which increases the pole area and provides an effect of increasing the driving force of the plunger 140. In particular, by employing such a configuration, the plunger driving force increases when there is a greater core-plunger distance, which makes it possible to obtain an even more level state in the range (indicated by the letter A in FIG. 7) in which the correlation relationship between the core-plunger distance and the plunger driving force appearing in the graph in FIG. 7 is comparatively level; this further reduces differences in the driving force depending on the distance, which provides an effect of making it easier to carry out flow rate control.

Third Variation

Figure 20:
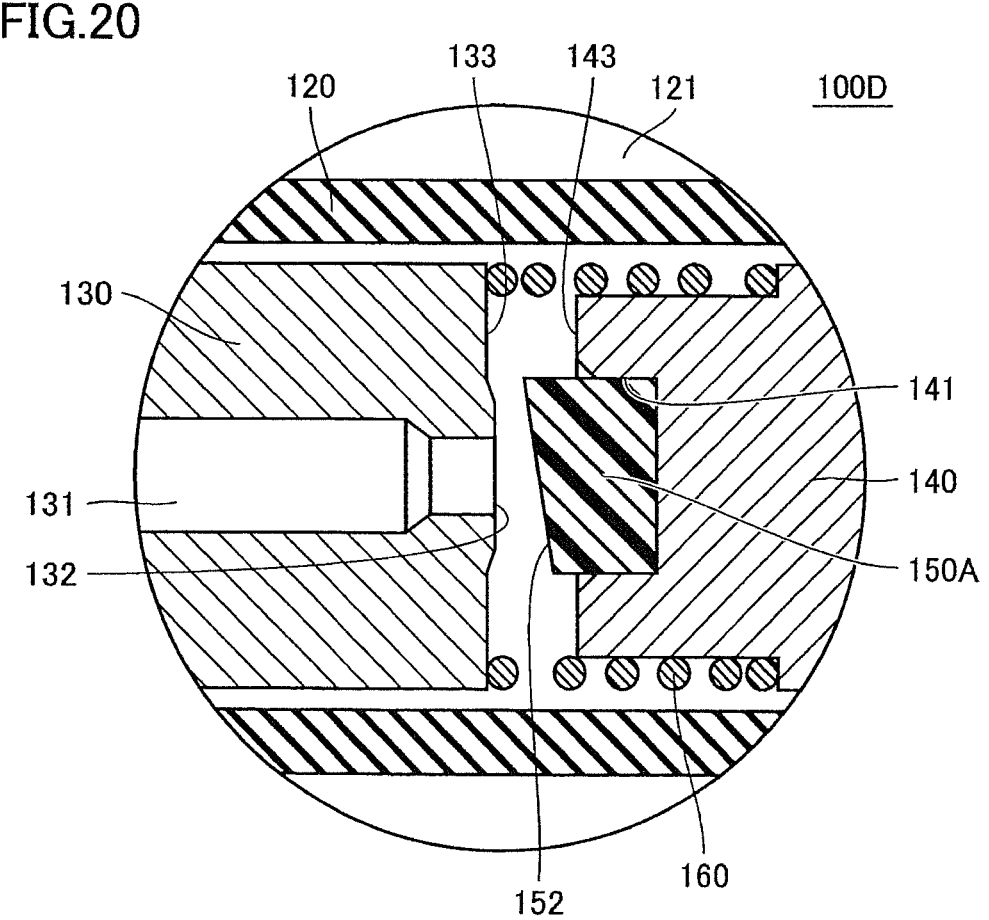
FIG. 20 is an enlarged cross-sectional view of primary components of a flow control valve according to a third variation on the first embodiment of the present invention.

FIG. 20 is an enlarged cross-sectional view of primary components of a flow control valve according to a third variation on the present embodiment. A flow control valve 100D according to the third variation on the present embodiment will be described next with reference to FIG. 20.

As shown in FIG. 20, the flow control valve 100D according to the third variation differs from the flow control valve 100A according to the aforementioned present embodiment in terms of the shape of the valve body 150A. Specifically, in the flow control valve 100D according to the third variation, the main surface of the valve body 150A that blocks the outflow port 132 is slanted, configuring the main surface as a slanted surface 152 that is non-parallel with the open face of the outflow port 132.

By employing such a configuration, not only can the effects described in the present embodiment above be achieved, but an effect in which even more precise flow rate control can be carried out is also achieved. That is, by employing this configuration, a state in which the outflow port 132 is completely closed by the valve body 150A making contact with a peripheral edge of the outflow port 132, elastically deforming, and sealing that peripheral edge, a state in which the valve body 150A does not make contact with the peripheral edge of the outflow port 132 and the outflow port 132 is allowed to communicate with the space between the plunger 140 and the core 130 over a comparatively wide area, and a state that is between these two states, in which the valve body 150A makes contact with the peripheral edge but the outflow port 132 is not completely blocked, and the outflow port 132 is allowed to communicate with the stated space over a comparatively narrow area, can be realized in the limited flow state, which makes more precise flow rate control possible.

Note that in addition to slanting the main surface of the valve body 150A as described above, a variety of other configurations can be considered as configurations for making precise flow rate control easy to perform, such as slanting the open face of the outflow port 132, providing different slants in the main surface of the valve body 150A and the open face of the outflow port 132, and so on.

Fourth Variation

Figure 21:
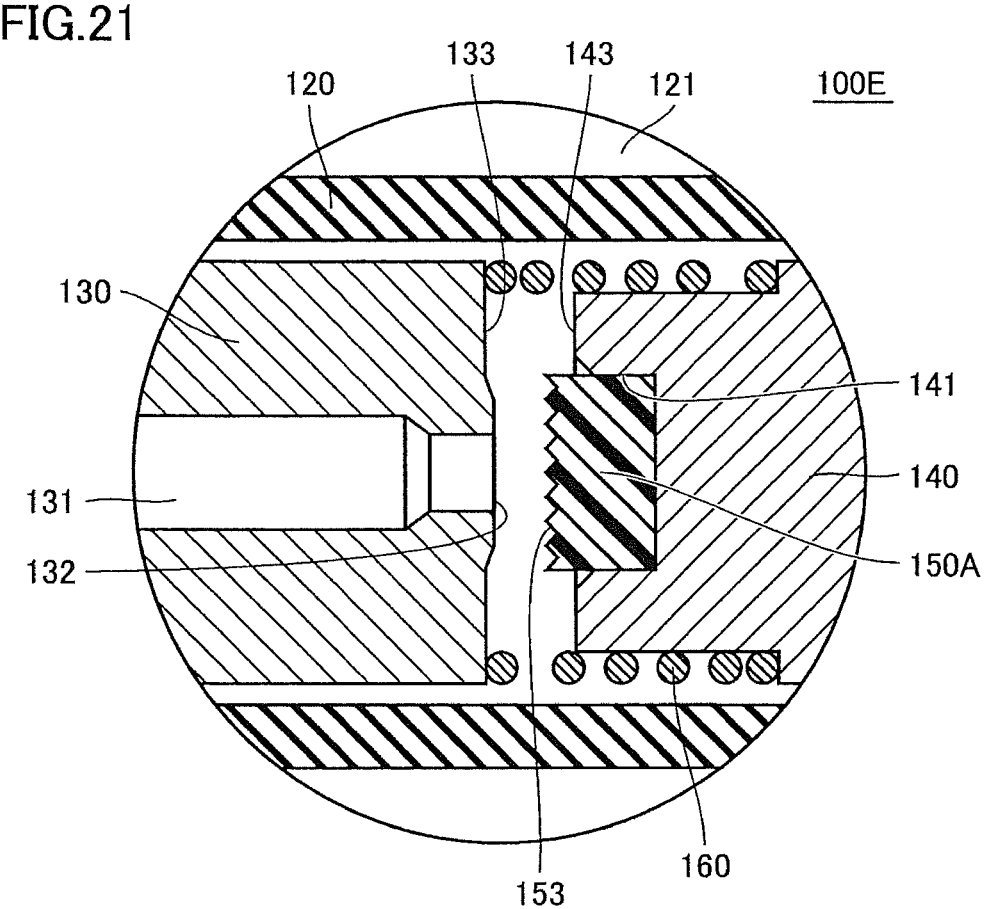
FIG. 21 is an enlarged cross-sectional view of primary components of a flow control valve according to a fourth variation on the first embodiment of the present invention.

FIG. 21 is an enlarged cross-sectional view of primary components of a flow control valve according to a fourth variation on the present embodiment. A flow control valve 100E according to the fourth variation on the present embodiment will be described next with reference to FIG. 21.

As shown in FIG. 21, the flow control valve 100E according to the fourth variation differs from the flow control valve 100A according to the aforementioned present embodiment in terms of the shape of the valve body 150A. Specifically, in the flow control valve 100E according to the fourth variation, the main surface of the valve body 150A that blocks the outflow port 132 is provided with minute non-planarities 153 so as to configure the main surface as a non-planar surface.

By employing such a configuration, not only can the effects described in the present embodiment above be achieved, but an effect in which even more precise flow rate control can be carried out is also achieved. That is, by employing this configuration, a state in which the outflow port 132 is completely closed by the valve body 150A making contact with the peripheral edge of the outflow port 132, elastically deforming, and the ridges of the minute non-planarities compressing and deforming so that the valve body 150A comes into tight contact with the peripheral edge, a state in which the valve body 150A does not make contact with the peripheral edge of the outflow port 132 and the outflow port 132 is allowed to communicate with the space between the plunger 140 and the core 130 over a comparatively wide area, and a state that is between these two states, in which the ridges of the minute non-planarities make contact with the peripheral edge but the outflow port 132 is not completely blocked, and the outflow port 132 is allowed to communicate with the stated space over a comparatively narrow area, can be realized in the limited flow state, which makes more precise flow rate control possible.

Fifth Variation

Figure 22:
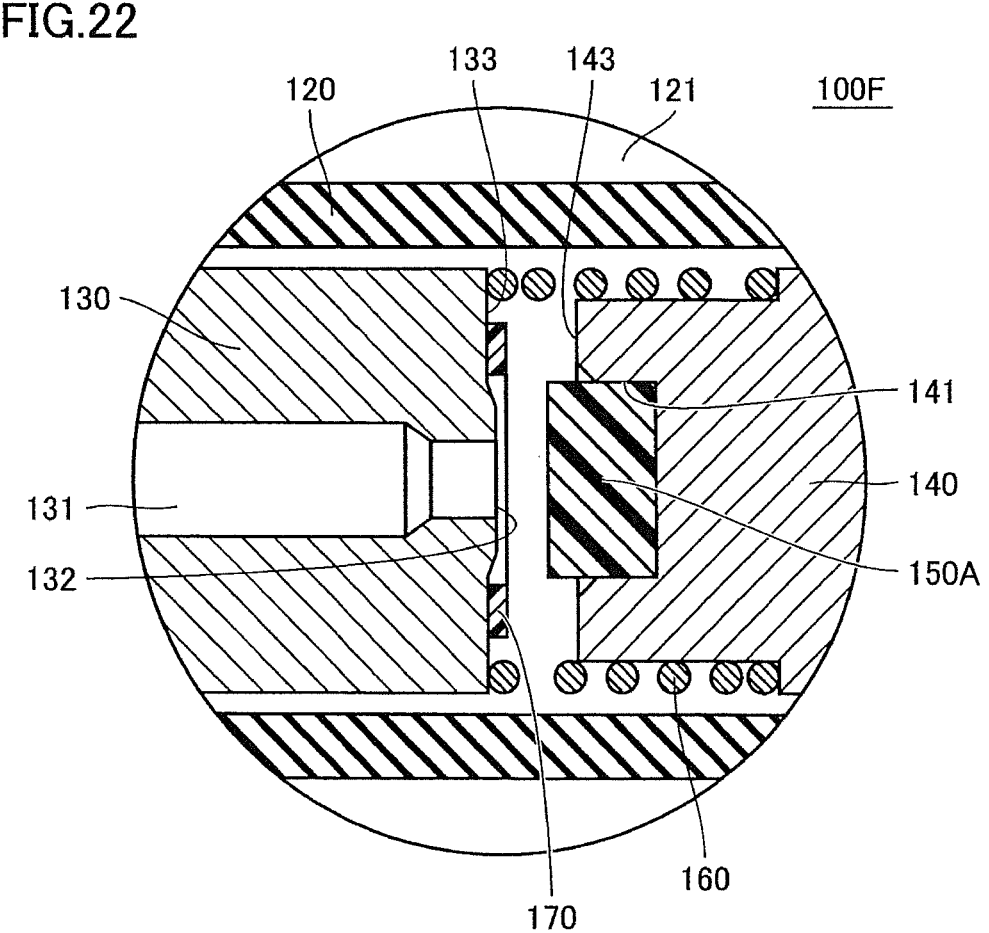
FIG. 22 is a schematic cross-sectional view of a flow control valve according to a fifth variation on the first embodiment of the present invention.

FIG. 22 is an enlarged cross-sectional view of primary components of a flow control valve according to a fifth variation on the present embodiment. A flow control valve 100F according to the fifth variation on the present embodiment will be described next with reference to FIG. 22.

As shown in FIG. 22, the flow control valve 100F according to the fifth variation differs from the flow control valve 100A according to the aforementioned present embodiment in that a spacer 170 is incorporated into the axial direction end surface 133 of the core 130. Specifically, the spacer 170 is a ring-shaped member configured of a nonmagnetic material, and is configured of a resinous or rubber member as exemplified by polyethylene terephthalate resin, silicone rubber, nitrile rubber, or the like, for example. The spacer 170 is affixed to the axial direction end surface 133 of the core 130 using an adhesive or the like so as to encircle the outflow port 132.

The spacer 170 is a member for ensuring that the core 130 and the plunger 140 do not come into contact with each other, and is configured having a thickness less than or equal to the distance between the core 130 and the plunger 140 when the valve body 150A blocks the outflow port 132.

By employing such a configuration, an effect of ensuring that the core 130 and the plunger 140 do not come into contact with each other can be achieved, in addition to the effects described in the aforementioned present embodiment. Accordingly, when the outflow port 132 is blocked by the valve body 150A, the plunger 140 can be prevented from coming into contact and affixing to the core 130 with certainty, and thus the precise flow rate control can be carried out in a more stable and certain manner.

Note that as long as the spacer 170 is disposed between the core 130 and the plunger 140, the spacer 170 may be incorporated into the axial direction end surface 143 of the plunger 140, and the spacer 170 may be configured of a member that does not have a ring shape. Furthermore, the method of attachment is not limited to using an adhesive, and another method may be used instead.

Sixth Variation

Figure 23:
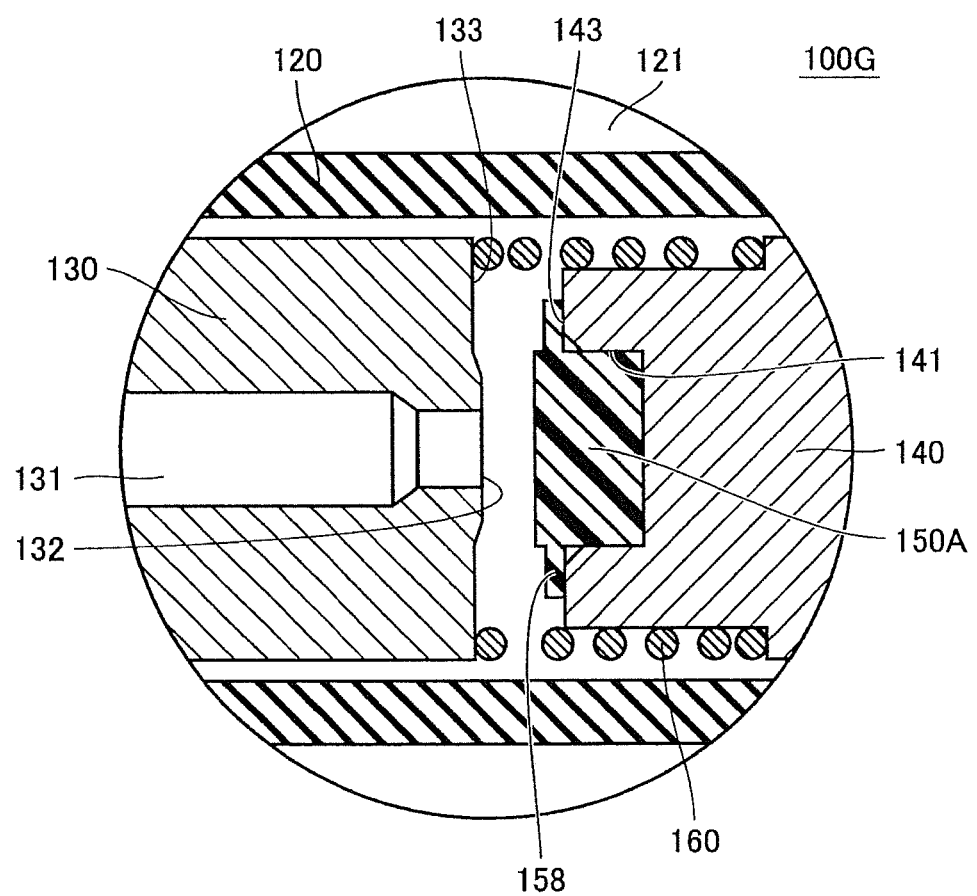
FIG. 23 is a schematic cross-sectional view of a flow control valve according to a sixth variation on the first embodiment of the present invention.

FIG. 23 is an enlarged cross-sectional view of primary components of a flow control valve according to a sixth variation on the present embodiment. A flow control valve 100G according to the sixth variation on the present embodiment will be described next with reference to FIG. 23.

As shown in FIG. 23, the flow control valve 100G according to the sixth variation differs from the flow control valve 100A according to the aforementioned present embodiment in that a spacer portion 158 extending outward is provided in the circumferential surface of the valve body 150A. Here, the spacer portion 158 is provided so as to be positioned on the axial direction end surface 143 of the plunger 140, and may have a ring shape as shown in FIG. 23, or may be formed having a non-ring shape.

The spacer portion 158 is a member for ensuring that the core 130 and the plunger 140 do not come into contact with each other, and is configured having a thickness less than or equal to the distance between the core 130 and the plunger 140 when the valve body 150A blocks the outflow port 132.

By employing such a configuration, an effect of ensuring that the core 130 and the plunger 140 do not come into contact with each other can be achieved, in addition to the effects described in the aforementioned present embodiment. Accordingly, when the outflow port 132 is blocked by the valve body 150A, the plunger 140 can be prevented from coming into contact and affixing to the core 130 with certainty, and thus the precise flow rate control can be carried out in a more stable and certain manner.

Seventh Variation

Figure 24:
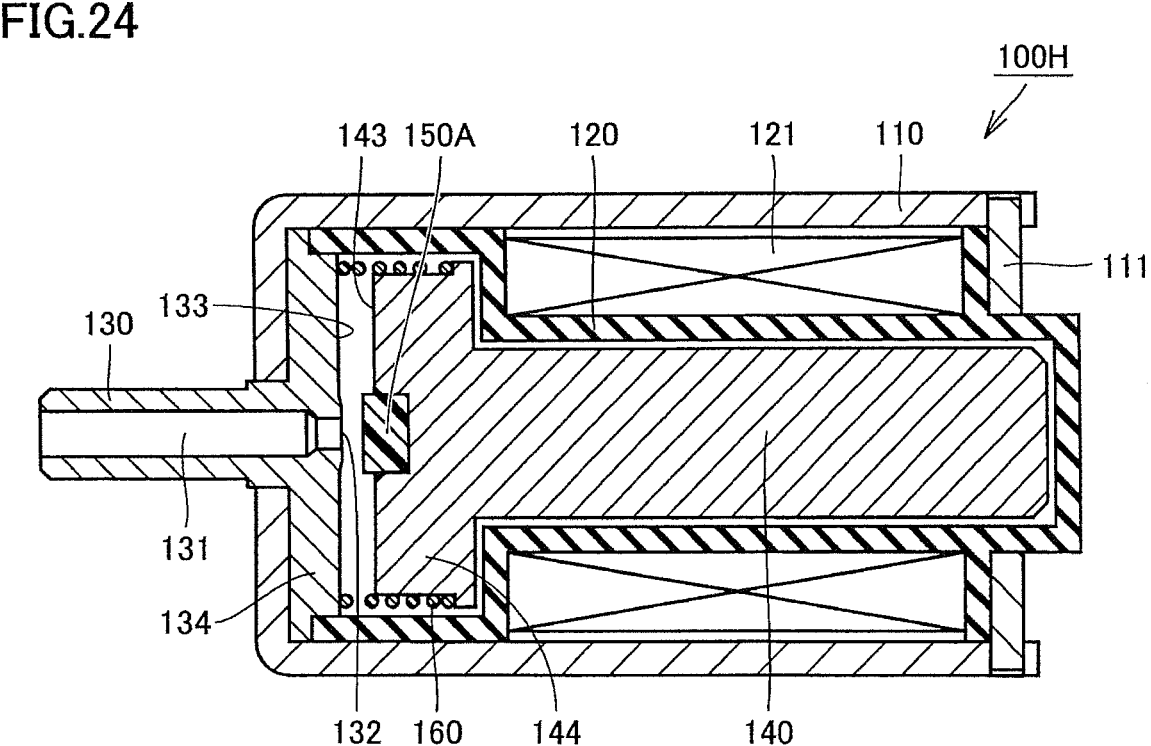
FIG. 24 is a schematic cross-sectional view of a flow control valve according to a seventh variation on the first embodiment of the present invention.

FIG. 24 is an enlarged cross-sectional view of primary components of a flow control valve according to a seventh variation on the present embodiment. A flow control valve 100H according to the seventh variation on the present embodiment will be described next with reference to FIG. 24.

As shown in FIG. 24, the flow control valve 100H according to the seventh variation differs from the flow control valve 100A according to the aforementioned present embodiment in that the shapes and so on of the bobbin 120, the core 130, and the plunger 140 are partially different. Specifically, in the flow control valve 100H according to the seventh variation, an axial direction end portion of the bobbin 120 extends in the axial direction of the flow control valve 100H toward the side on which the core 130 is located, and flange portions 134 and 144 are provided in the core 130 and the plunger 140 so as to be positioned within the portion of the bobbin 120 that is extended.

Here, the solenoid coil 121 is not disposed in the portion of the bobbin 120 that is extended, and thus the interior of the bobbin 120 in that portion has a wider space in the radial direction than the interior of the bobbin 120 where the solenoid coil 121 is disposed. Accordingly, the flange portions 134 and 144 can be disposed within the interior of that portion, and as a result, the axial direction end surface 133 of the core 130 and the axial direction end surface 143 of the plunger 140 are disposed in this portion. Note that the spring 160 serving as the biasing member is also disposed within the portion in which the bobbin 120 extends.

By employing such a configuration, not only can the effects described above in the present embodiment be obtained, but the surface area between the axial direction end surface 133 of the core 130 and the axial direction end surface 143 of the plunger 140, which is a region through which a magnetic flux flows during electrification, can also be increased, which increases the pole area and provides an effect of increasing the driving force of the plunger 140.

Second Embodiment

Figure 25:
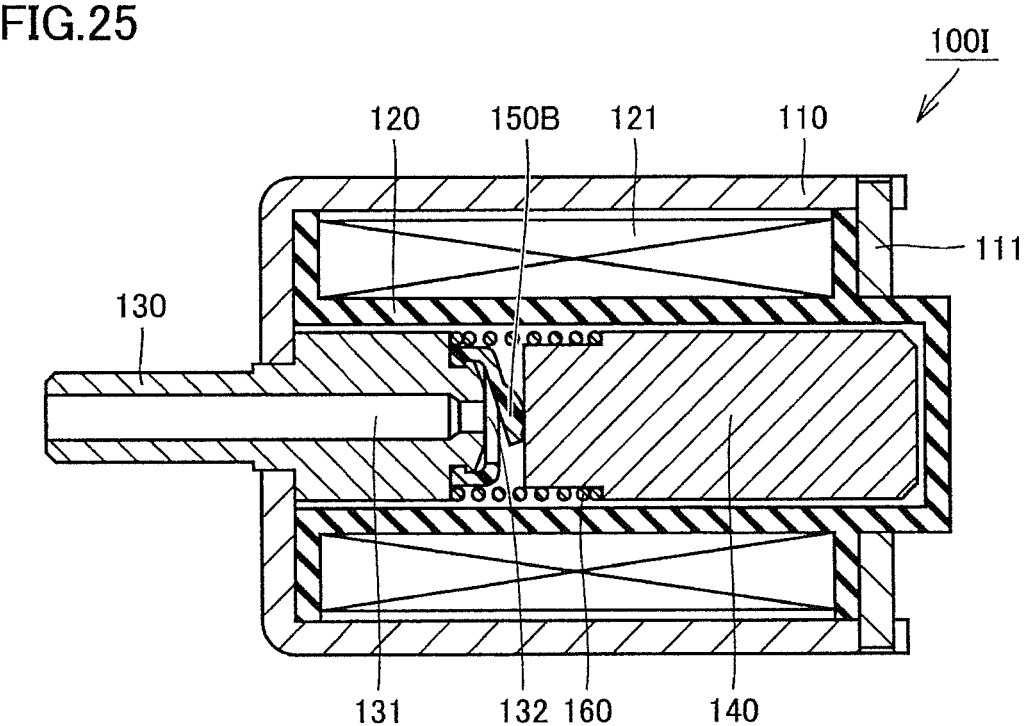
FIG. 25 is a schematic cross-sectional view of a flow control valve according to a second embodiment of the present invention.
Figure 26:
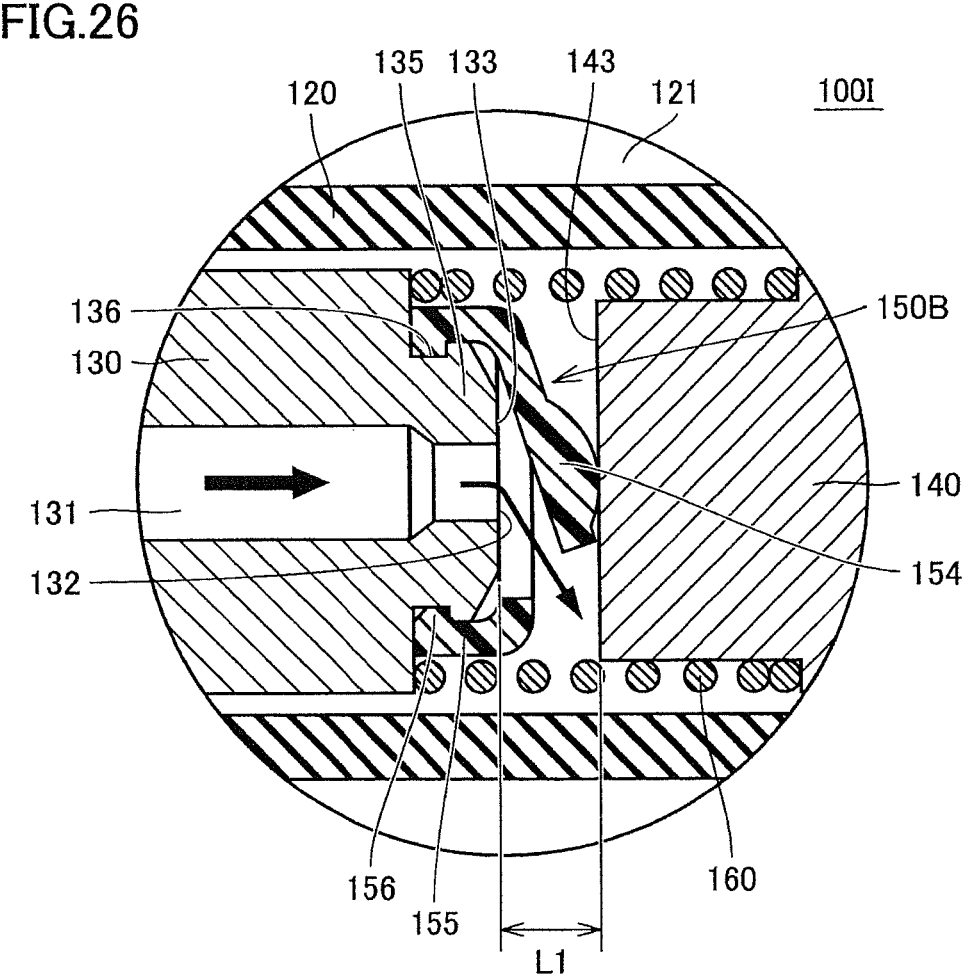
FIG. 26 is an enlarged cross-sectional view of primary components, illustrating the flow control valve shown in FIG. 25 in an open state.
Figure 27:
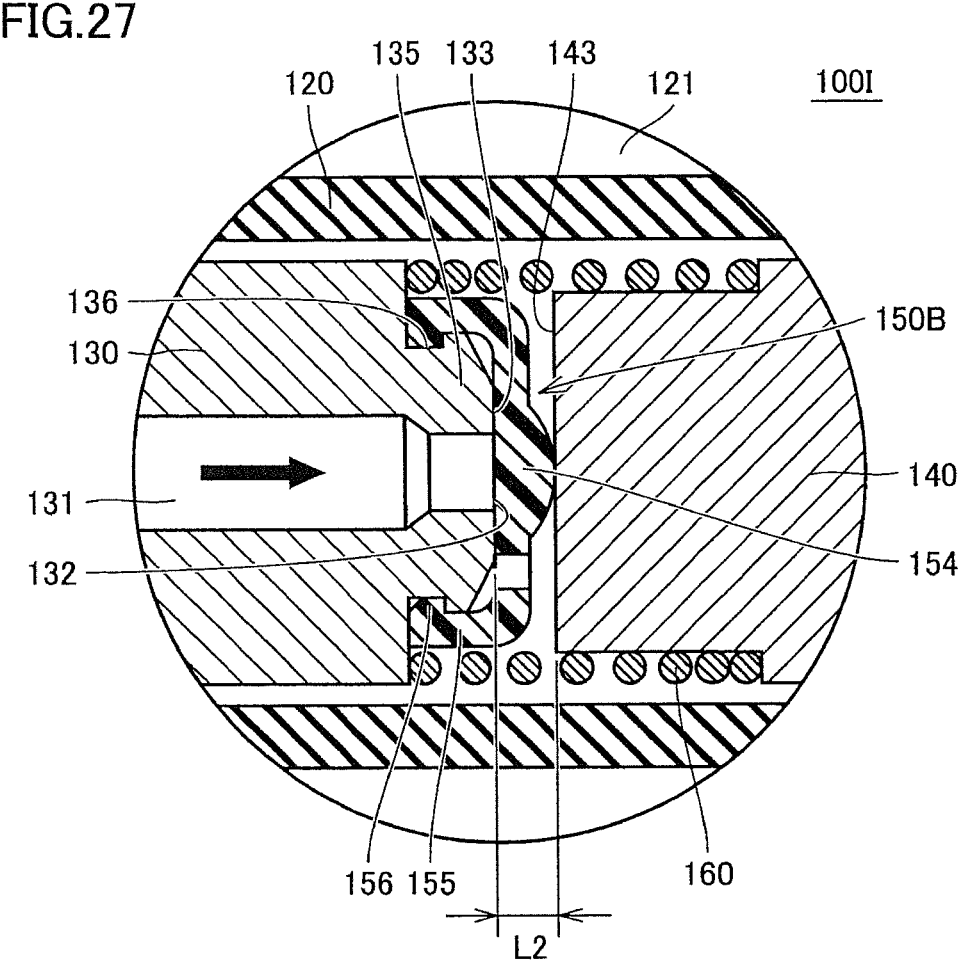
FIG. 27 is an enlarged cross-sectional view of primary components, illustrating the flow control valve shown in FIG. 25 in a closed state.
Figure 28:
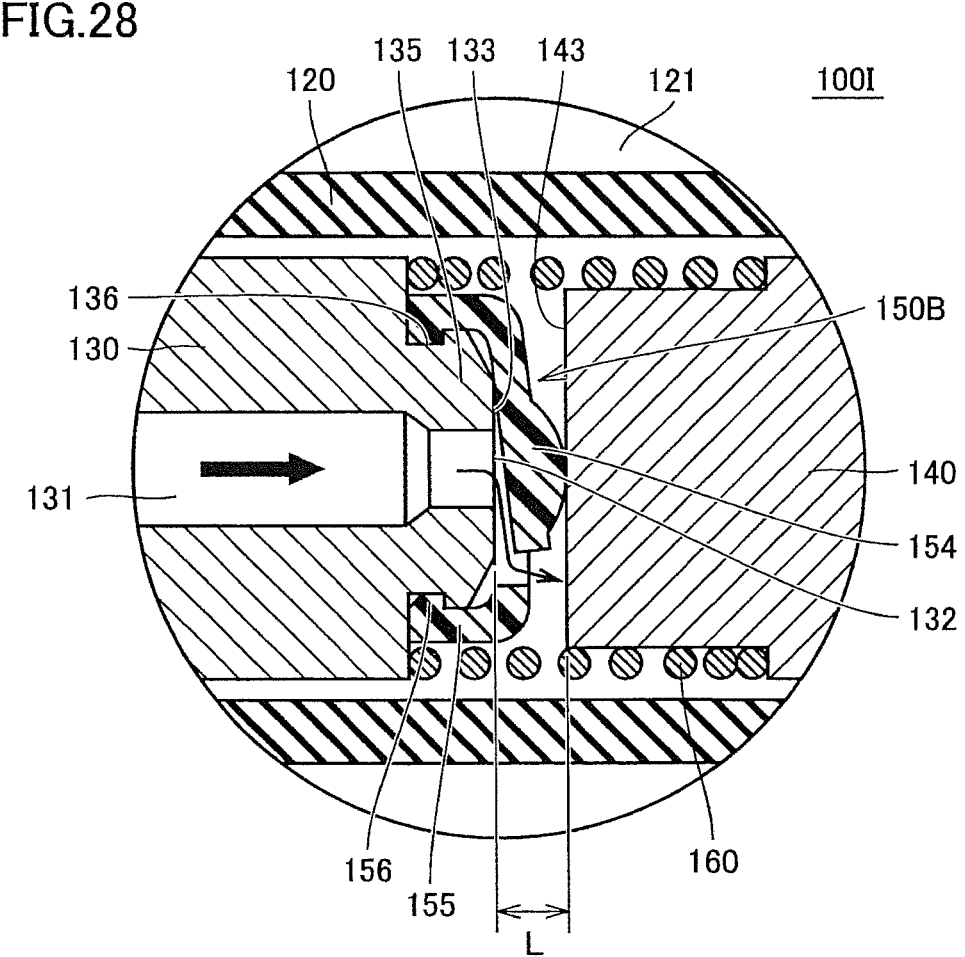
FIG. 28 is an enlarged cross-sectional view of primary components, illustrating the flow control valve shown in FIG. 25 in a limited flow state.

FIG. 25 is a schematic cross-sectional view of a flow control valve according to a second embodiment of the present invention. FIGS. 26 through 28, meanwhile, are enlarged cross-sectional views of primary components, illustrating operations of the flow control valve according to the present embodiment. Here, FIG. 26 illustrates the flow control valve in an open state, FIG. 27 illustrates the flow control valve in a closed state, and FIG. 28 illustrates the flow control valve in a limited flow state. Next, a specific configuration and operations of a flow control valve 100I according to the present embodiment will be described with reference to FIGS. 25 through 28. Note that the flow control valve 100I according to the present embodiment is a normally-open solenoid-type flow control valve, like the flow control valve 100A according to the aforementioned first embodiment.

Although the flow control valve 100A according to the first embodiment of the present invention as described above is configured so that the valve body 150A is incorporated into the plunger 140, in the flow control valve 100I according to the present embodiment, a valve body 150B is provided in the core 130, as shown in FIG. 25.

As shown in FIG. 25, the core 130 includes a protruding portion 135 in the end portion thereof on the side on which the plunger 140 is located, and the nozzle portion 131 formed within the core 130 is provided so as to pass through the interior of the protruding portion 135. As a result, the outflow port 132 is disposed in the axial direction end surface 133 of the protruding portion 135 located on the side toward the plunger 140. Meanwhile, an engagement recess portion 136 is provided in the outer circumferential surface of the protruding portion 135.

The axial direction end surface 143 of the plunger 140 is configured as a flat surface, and the housing recess portion 141, which is provided in the flow control valve 100A according to the aforementioned first embodiment of the present invention, is not provided.

The valve body 150B is an elastic member configured of silicone rubber or the like, for example, and is incorporated into the core 130 so as to cover the protruding portion 135 of the core 130. The valve body 150B includes a valve portion 154 having a predetermined shape and a support portion 155 having an approximately cylindrical shape. The valve portion 154 and the support portion 155 are formed in an integrated manner through injection molding or the like, for example.

The support portion 155 is a member for incorporating the valve body 150B into the core 130, and an engagement protruding portion 156 is provided in the inner circumferential surface thereof. The valve body 150B is incorporated into the core 130 by the engagement protruding portion 156 engaging with the aforementioned engagement recess portion 136.

The valve portion 154 extends from a predetermined area in the circumferential direction of the support portion 155, which has an approximately cylindrical shape, and blocks or opens the outflow port 132 by bending and deforming. Here, the valve portion 154 is configured so that in a no-load state, the outflow port 132 is open; the valve portion 154 blocks the outflow port 132 by being pressed by the axial direction end surface 143 of the plunger 140 in the axial direction of the flow control valve 100I.

As shown in FIG. 26, when the flow control valve 100I is not operating, the solenoid coil 121 is not electrified and is in a non-electrified state, and thus a magnetic circuit is not formed. Accordingly, the plunger 140 is not pulled toward the core 130, and, due to the biasing force of the spring 160, is located at a position distanced from the core 130 in the axial direction of the flow control valve 100I by a predetermined distance L1. If the position of the valve portion 154 of the valve body 150B at that time is taken as a first position, the first position is a position in which the valve portion 154 is distanced from the outflow port 132 by a predetermined distance.

In this state, the outflow port 132 is not blocked by the valve portion 154 of the valve body 150B, and is in a fully open state. Accordingly, compressed air present within the pressurizing air bladder 42 that communicates with the nozzle portion 131 is exhausted via the outflow port 132 to a space located between the core 130 and the plunger 140, and is furthermore exhausted to the exterior of the flow control valve 100I via a gap between the bobbin 120 and the plunger 140.

As shown in FIGS. 27 and 28, when the flow control valve 100I is operating, the solenoid coil 121 is electrified and is thus in an electrified state; as a result, a magnetic circuit is formed, with a magnetic flux passing through the frame 110, the core 130, the plunger 140, and the base 111. Accordingly, the plunger 140 is pulled toward the core 130 in the axial direction of the flow control valve 100I, against the biasing force of the spring 160.

As shown in FIG. 27, in the case where the current applied to the solenoid coil 121 is greater than or equal to a predetermined value, the plunger 140 is pulled to a maximum extent toward the core 130 in the axial direction, and the valve portion 154 of the valve body 150B is pressed against the core 130 by the plunger 140 so as to make contact with the core 130; as a result, the outflow port 132 is completely blocked by the valve body 150B and is thus completely closed. In this state, the compressed air is completely prevented from flowing out via the outflow port 132, and thus the internal pressure in the pressurizing air bladder 42 is maintained. Note that the position of valve portion 154 of the valve body 150B at this time is a second position.

The flow control valve 100I according to the present embodiment is configured so that when the valve portion 154 of the valve body 150B is in the second position and completely blocks the outflow port 132, the plunger 140 is not in contact with the core 130; as a result, in this state, the plunger 140 is located in a position distanced from the core 130 in the axial direction of the flow control valve 100I by a predetermined distance L2. This is primarily due to the protruding portion 135 of the core 130 being covered by the valve body 150B, as described above.

Meanwhile, as shown in FIG. 28, in the case where the current applied to the solenoid coil 121 is less than the predetermined value, the plunger 140 is pulled to a certain extent toward the core 130 in the axial direction; the distance L between the core 130 and the plunger 140 takes on a value that is lower than the aforementioned distance L1 and greater than the aforementioned distance L2. Accordingly, the valve portion 154 of the valve body 150B is disposed between the aforementioned first position and second position.

In this state, the valve portion 154 of the valve body 150B does not completely block the outflow port 132, but the distance therebetween has decreased and thus the outflow port 132 is blocked to a certain extent. Accordingly, although the compressed air does flow out via the outflow port 132, the compressed air is prevented by the valve portion 154 of the valve body 150B from flowing out from the outflow port 132 to a certain extent, and the outflow rate is thus limited.

Here, a distance between the open face of the outflow port 132 and a primary surface of the valve portion 154 of the valve body 150B located on the side toward the outflow port 132 is determined by the distance L between the core 130 and the plunger 140, and the distance L is adjusted in a variable manner by controlling the magnitude of the current applied to the solenoid coil 121. Accordingly, by adjusting the driving voltage of the flow control valve 100I in order to adjust the distance L, the flow rate of the compressed air flowing out from the outflow port 132 can be adjusted in a variable manner.

Accordingly, by employing the flow control valve 100I according to the present embodiment, precise flow rate control, which has been difficult conventionally, can be carried out, in the same manner as with the flow control valve 100A according to the aforementioned first embodiment. Accordingly, by employing a blood pressure monitor that uses the flow control valve 100I as an exhaust valve, the internal pressure of the pressurizing air bladder 42 can be controlled precisely, and it is also unnecessary to provide a separate flow rate control mechanism, which makes it possible to realize a simple configuration.

Although the aforementioned embodiments of the present invention and the variations thereon describe cases where the fluid subject to flow rate control is compressed air as examples, embodiments of the present invention are not limited to such an application, and the fluid subject to flow rate control may be a high-pressure gas aside from compressed air, a compressed liquid, or the like.

Furthermore, the characteristic configurations described in the aforementioned embodiments of the present invention and the variations thereon can of course be combined with each other as necessary.

Furthermore, although the aforementioned embodiments of the present invention and the variations thereon describe an upper arm blood pressure monitor, which measures blood pressure values such as the systolic blood pressure value, the diastolic blood pressure value, and so on, as an example of the blood pressure information measurement device, one or more embodiments of the present invention can of course also be applied in a wrist blood pressure monitor or a leg blood pressure monitor, as well as in blood pressure information measurement devices capable of measuring a pulse wave, a pulse, an indicator of artery hardness as exemplified by an AI (augmentation index) value, an average blood pressure value, oxygen saturation, and so on.

In this manner, the embodiments disclosed herein are to be understood in all ways as exemplary and in no ways limiting. The technical scope of the present invention is defined by the appended claims, and all variations that fall within the meaning and range of equivalency of the claims are intended to be embraced therein.

REFERENCE NUMERALS LIST 1 blood pressure monitor
10 main body
20 control unit
21 display unit
22 memory unit
23 operating unit
24 power source unit
30 pressurizing air system component
31 pressure pump
33 pressure sensor
34 pressure pump driving circuit
35 flow control valve driving circuit
36 oscillation circuit
40 cuff
41 outer cover
42 pressurizing air bladder
50 air tube
51 connection tube
100A-100I flow control valve
110 frame
111 base
120 bobbin
121 solenoid coil
130 core
131 nozzle portion
132 outflow port
133 axial direction end surface
134 flange portion
135 protruding portion
136 engagement recess portion
140 plunger
141 housing recess portion
142 engagement recess portion
143 axial direction end surface
144 flange portion
150A, 150B valve body
151 engagement protruding portion
152 slanted surface
153 minute non-planarities
154 valve portion
155 support portion
156 engagement protruding portion
158 spacer portion
160 spring
170 spacer

The invention claimed is:

1. A flow control valve capable of controlling a flow rate of a fluid in a variable manner, the flow control valve comprising:
a solenoid coil that generates a magnetic flux;
a bobbin around which the solenoid coil is wound;
a plunger inserted into the bobbin so as to be capable of sliding by a force caused by the magnetic flux generated by the solenoid coil;
a core in which is provided an outflow port from which the fluid flows;
a biasing mechanism configured to bias the plunger in a direction away from the core; and
a valve body disposed facing the outflow port,
wherein during a non-operating state in which the solenoid coil is not electrified, the valve body is disposed at a first position distanced from the outflow port,
wherein during an operating state in which the solenoid coil is electrified, a flow rate of the fluid flowing from the outflow port is adjusted by the valve body being moved in a direction toward the outflow port due to the plunger being driven against a biasing force of the biasing mechanism and a distance between the valve body and the outflow port changes as a result,
wherein, during the operating state in which the solenoid coil is further electrified, the valve body reaches a second position in which the valve body contacts the core to block the outflow port, but a surrounding portion of the plunger surrounding the valve body is not in contact with the core to provide a gap between the surrounding portion of the plunger and the core,
wherein the gap is greater than or equal to 0.2 millimeters (mm),
wherein the valve body is incorporated into the plunger by being affixed to a main surface of the plunger that faces the core,
wherein the valve body comprises a protrusion that protrudes toward the core beyond the main surface of the plunger that faces the core,
wherein the protrusion blocks the outflow port at the second position,
wherein the protrusion is not in contact with the core at the first position,
wherein a cross sectional area of the protrusion is less than a cross sectional area of the plunger, and
wherein the valve body is configured as an elastic member.

2. The flow control valve according to claim 1, wherein when the valve body is at a third position in which the valve body controls the flow rate, the plunger is disposed between a position of the plunger when the valve body is at the first position and a position of the plunger when the valve body is at the second position.

3. A blood pressure information measurement device comprising:
the flow control valve according to claim 1 as an exhaust valve for reducing an internal pressure of a pressurizing fluid bladder for compressing a body.

4. The blood pressure information measurement device according to claim 3,
wherein during measurement, at least a systolic blood pressure value and a diastolic blood pressure value are calculated based on a deflation measurement method by controlling the driving of the flow control valve serving as the exhaust valve so that the internal pressure of the pressurizing fluid bladder decreases slowly, and wherein after the measurement is complete, the driving of the flow control valve serving as the exhaust valve is controlled so that the internal pressure of the pressurizing fluid bladder decreases rapidly.

5. The blood pressure information measurement device according to claim 3, wherein during measurement, at least a systolic blood pressure value and a diastolic blood pressure value are calculated based on an inflation measurement method by controlling the driving of the flow control valve serving as the exhaust valve so that the internal pressure of the pressurizing fluid bladder increases slowly, and wherein after the measurement is complete, the driving of the flow control valve serving as the exhaust valve is controlled so that the internal pressure of the pressurizing fluid bladder decreases rapidly.

* * * * *